US00PP28200P3

(12) United States Plant Patent
Mehlenbacher et al.

(10) Patent No.: US PP28,200 P3
(45) Date of Patent: Jul. 18, 2017

(54) ***CORYLUS* PLANT NAMED 'MCDONALD'**

(50) Latin Name: ***Corylus avellana* cultivar**
Varietal Denomination: McDonald

(71) Applicant: Oregon State University, Corvallis, OR (US)

(72) Inventors: Shawn A. Mehlenbacher, Corvallis, OR (US); David C. Smith, Corvallis, OR (US); Rebecca L. McCluskey, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 376 days.

(21) Appl. No.: 14/544,504

(22) Filed: Jan. 13, 2015

(65) Prior Publication Data

US 2016/0205823 P1 Jul. 14, 2016

(51) Int. Cl.
*A01H 5/08* (2006.01)

(52) U.S. Cl.
USPC ..... Plt./152

(58) Field of Classification Search
USPC ..... Plt./152
CPC ..... A01H 5/0825
See application file for complete search history.

(56) References Cited

PUBLICATIONS

Bassil et al, "Additional Microsatellite Markers of the European Hazelnut," *Acta Hortic*. 686:105-110, 2005.
Bassil et al, "Microsatellite Markers in Hazelnut: Isolation, Characterization, and Cross-species Amplification," *J. Amer. Soc. Hort. Sci.*, 130(4):543-549, 2005.
Bassil et al, "Nuclear and chloroplast microsatellite markers to assess genetic diversity and evolution in hazelnut species, hybrids and cultivars," *Genet. Resour. Crop Evol.*, 60(2):543-568, 2012.
Boccacci et al, "Characterization and evaluation of microsatellite loci in European hazelnut (*Corylus avellana* L.) and their transferability to other *Corylus* species," *Molecular Ecology Notes*, 5:934-937, 2005.
Boccacci et al, "DNA typing and genetic relations among European hazelnut (*Corylus avellana* L.) cultivars using microsatellite markers," *Genome*, vol. 49, pp. 598-611, 2006.
Gökirmak et al, "Characterization of European hazelnut (*Corylus avellana*) cultivars using SSR markers," *Genet. Resour. Crop Evol.*, vol. 56(2), pp. 147-172, 2008.
Gürcan et al, "Genetic diversity in hazelnut (*Corylus avellana* L.) cultivars from Black Sea countries assessed using SSR markers," *Plant Breeding*, 129:422-434, 2010.
Gürcan et al, "Development, characterization, segregation, and mapping of microsatellite markers for European hazelnut (*Corylus avellana* L.) from enriched genomic libraries and usefulness in genetic diversity studies," *Tree Genetics & Genomes*, vol. 6, pp. 513-531, 2010.
Gürcan et al, "Transferability of Microsatellite Markers in the Betulaceae," *J. Amer. Soc. Hort. Sci.* 135(2), pp. 159-173, 2010.
Gürcan and Mehlenbacher. "Development of microsatellite marker loci for European hazelnut (*Corylus avellana* L.) from ISSR fragments," *Molecular Breeding* 26:551-559, 2010.
Mehlenbacher et al., "Inheritance of the Cutleaf Trait in Hazelnut," *HortScience*, 30(3):611-612, 1995.
Mehlenbacher et al., "'Tonda Pacifica' hazelnut," *HortScience* 46:505-508, 2011.
Mehlenbacher et al., "'Santiam' hazelnut," *HortScience* 42:715-717, 2007.
Mehlenbacher et al., "RAPD markers linked to eastern filbert blight resistance in *Corylus avellana," Theor. Appl. Genet.*, 108:651-656, 2004.
Sathuvalli et al., "Characterization of American hazelnut (*Corylus americana*) accessions and *Corylus americana*×*Corylus avellana* hybrids using microsatellite markers," *Genet. Resour. Crop. Evol.*, 59:1055-1075, 2012.

*Primary Examiner* — Kent L Bell
(74) *Attorney, Agent, or Firm* — Klarquist Sparkman, LLP

(57) ABSTRACT

A new and distinct *Corylus* plant named 'McDonald' characterized by moderate vigor and upright-spreading plant habit, yellowish-green developing and fully expanded leaves during the spring and summer, resistance to eastern filbert blight caused by the fungus *Anisogramma anomala* (Peck) E. Müller, presence of random amplified polymorphic DNA markers 152-800 and 268-580 in DNA, expression of incompatibility alleles $S_2$ and $S_{15}$ in the styles, and DNA fingerprints at 14 of 21 microsatellite marker loci differ from both parents, 'Tonda Pacifica' and 'Santiam', and from one parent at an additional 5 marker loci.

17 Drawing Sheets

1

ACKNOWLEDGMENT OF GOVERNMENT SUPPORT

This invention was made with government support under Specific Cooperative Agreement No. 58-5358-4542 awarded by the United States Department of Agriculture. The government has certain rights in the invention.

Botanical denomination: *Corylus avellana* cultivar.

Variety designation: 'McDonald'.

2

BACKGROUND

The present Invention relates to a new and distinct cultivar of *Corylus* plant, botanically known as *Corylus avellana*, and hereinafter referred to by the name 'McDonald'.

The new *Corylus* resulted from a controlled cross of female parent 'Tonda Pacifica' (U.S. Plant Pat. No. 22,715) and male parent 'Santiam' (unpatented) made in 1997. Hybrid seeds from the cross were harvested in August 1997, stratified, and seedlings grown in the greenhouse during the summer of 1998. From this cross, a total of 132 seedling trees were planted in the field in Corvallis in October, 1998. 'McDonald' was discovered and selected as a single plant within the progeny of the stated cross-pollination in a controlled environment in Corvallis, Oreg., USA. It was originally assigned the designation OSU 880.027, which indicates the row and tree location of the original seedling.

'Tonda Pacifica' (OSU 228.084) was released in 2010 (Mehlenbacher et al., 2011), is from a cross of 'Tonda Gentile delle Langhe'×OSU 23.024 (='Barcelona'×'Extra Ghiaghli'). 'Santiam' (Mehlenbacher et al., 2007), released in 2005, carries a dominant allele for a very high level of resistance to eastern filbert blight (EFB) from 'Gasaway' (unpatented). 'Tonda Gentile delle Langhe' (unpatented), the female parent of 'Tonda Pacifica', is an important cultivar in Piemonte, northern Italy. 'Barcelona' (unpatented), Oregon's most widely planted hazelnut cultivar, is known as 'Castanyera' where it originated in Catalunya, Spain. 'Extra Ghiaghli' (unpatented), obtained from Greece, is a clone of the important Turkish cultivar 'Tombul'. 'Gasaway' (unpatented) is the source of a single dominant gene for resistance to eastern filbert blight.

The new cultivar was asexually reproduced by rooted suckers annually for nine years (2004-2005, 2007-2013) in Corvallis, Oreg. The new cultivar was also asexually propagated by whip grafting in 2005 in Corvallis, Oreg. The unique features of this new *Corylus* are stable and reproduced true-to-type in successive generations of asexual reproduction.

SUMMARY

The following traits have been observed and are determined to be the unique characteristics of 'McDonald'. These characteristics in combination distinguish 'McDonald' as a new and distinct cultivar:

1. Moderate vigor and upright-spreading plant habit.
2. Yellowish-green developing and fully expanded leaves during the spring and summer.
3. Resistance to eastern filbert blight caused by the fungus *Anisogramma anomala* (Peck) E. Müller.
4. Presence of random amplified polymorphic DNA markers 152-800 and 268-580 in DNA of 'McDonald' amplified by the polymerase chain reaction. These two markers are linked to a dominant allele for resistance to eastern filbert blight from the cultivar 'Gasaway' (unpatented).
5. Expression of incompatibility alleles $S_2$ and $S_{15}$ in the styles.
6. DNA fingerprints at 14 of 21 microsatellite marker loci differ from both parents, 'Tonda Pacifica' and 'Santiam', and from one parent at an additional 5 marker loci. Additional DNA fingerprints of grandparent 'Tonda Gentile delle Langhe', standard cultivar 'Barcelona', eastern filbert blight resistance source 'Gasaway' and five cultivars released by Oregon State University hazelnut breeding program are shown in Table 6.

Comparisons in two replicated trials conducted in Corvallis, Oreg., plants of the new *Corylus* differed from plants of the *Corylus avellana* cultivar 'Barcelona' and other cultivars and selections of *Corylus avellana* known to the Inventors primarily in nut size, nut shape, kernel percentage (ratio of kernel weight to nut weight), frequency of defects (blank nuts, moldy kernels, twins, etc.), time of pollen shed, time of nut maturity, length of the husk or involucre, and plant size. For example:

- Blank nut frequency: 'McDonald' 2.7% in first trial, 5.1% in second trial, %, 'Barcelona' 7.7% in first trial and 7.1% in second trial;
- Pollen shed: 'McDonald' sheds pollen with 'Dorris', 'Wepster' and 'Yamhill', slightly later than 'Tonda Pacifica', and slightly earlier than 'Sacajawea', 'Yamhill' and 'York'. 'McDonald' descriptor=5;
- Nut maturity: 'McDonald' nuts mature 14 days earlier than 'Barcelona'; and
- Husk Length: 'McDonald' 1.5 times nut length, same as 'Barcelona', while 'Wepster' is 2 times nut length.

'McDonald' is well-suited to the blanched kernel market for use in chocolate products and baked goods. 'McDonald' combines high nut yield, early nut maturity, small round nuts and kernels, high kernel percentage, good kernel blanching and excellent flavor. The tree is moderately vigorous and has a desirable growth habit.

DNA markers and field observations indicate that 'McDonald' has a very high level of resistance to eastern filbert blight (EFB) caused by the fungus *Anisogramma anomala* (Peck) E. Müller. The resistance is conferred by a dominant allele from 'Gasaway'. EFB is now present throughout the Willamette Valley where 99% of the U.S. hazelnut crop is grown. Pruning to remove cankers and fungicide applications are currently used to manage the disease in orchards of 'Barcelona' and other susceptible cultivars. Thus, 'McDonald' is suitable for planting in areas with high disease pressure, as are previous releases 'Santiam' (2005), 'Yamhill' (2008, unpatented), 'Jefferson' (2009, unpatented), 'Dorris' (2012, U.S. Plant Pat. No. 25,022) and 'Wepster' (2013, U.S. Plant Pat. No. 27,141). 'Wepster', released as a cultivar in 2013, is cross-compatible with 'McDonald' in both directions. Thus 'Wepster' and 'McDonald' can be planted together with each serving as a pollinizer for the other.

BRIEF DESCRIPTION OF THE DRAWINGS

The accompanying colored photographs illustrate the overall appearance of the new cultivar, showing the colors as true as it is reasonably possible to obtain in colored reproductions of this type. Foliage colors in the photographs may differ slightly from the color values cited in the detailed botanical description which accurately describe the colors of the new *Corylus*.

FIGS. 12A-12B show a phenology chart showing time of female receptivity (bottom, red) and pollen shed (top, green) of 'McDonald' (OSU 880.027) and other hazelnut cultivars (December 2011-March 2012).

FIGS. 13A-13D show a phenology chart showing bloom stage and pollen shed of hazelnut cultivars, pollinizers and selections (December 2012-March 2013).

DETAILED DESCRIPTION

Figure 1:
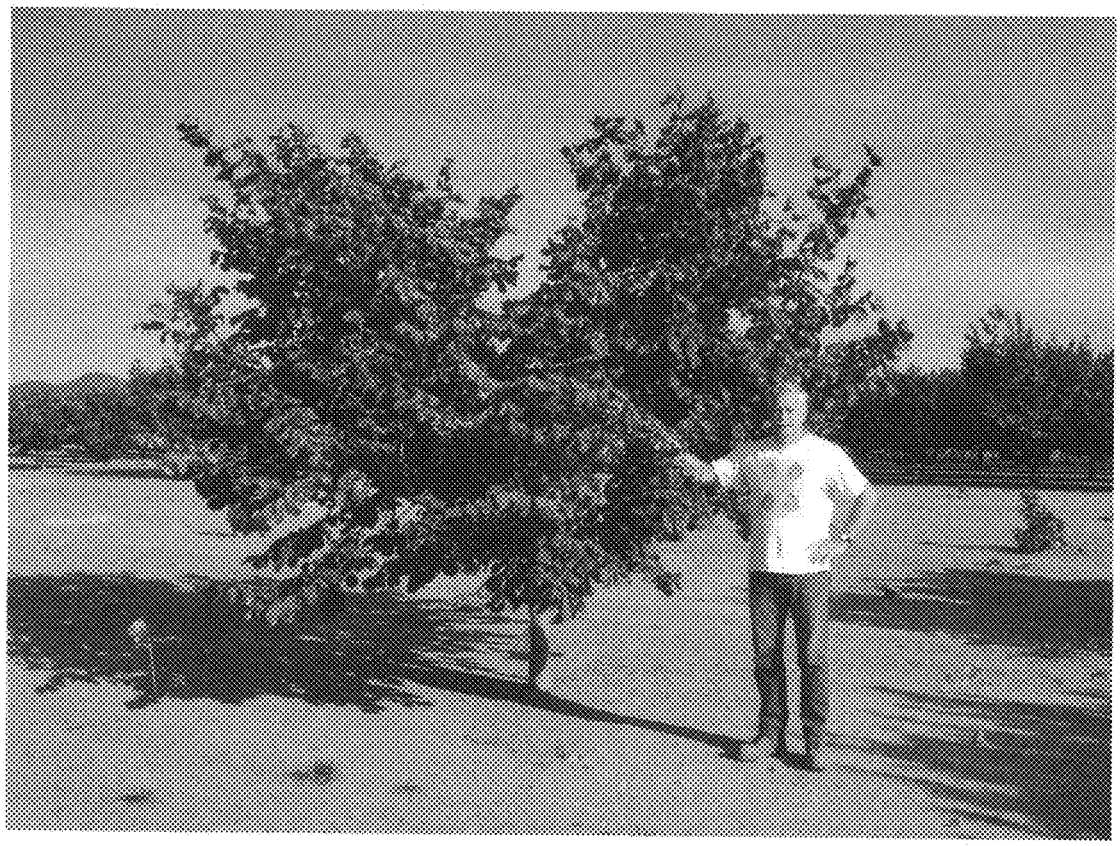
FIG. 1 shows a tree the new cultivar 'McDonald' hazelnut in the 8th leaf.
Figure 2:
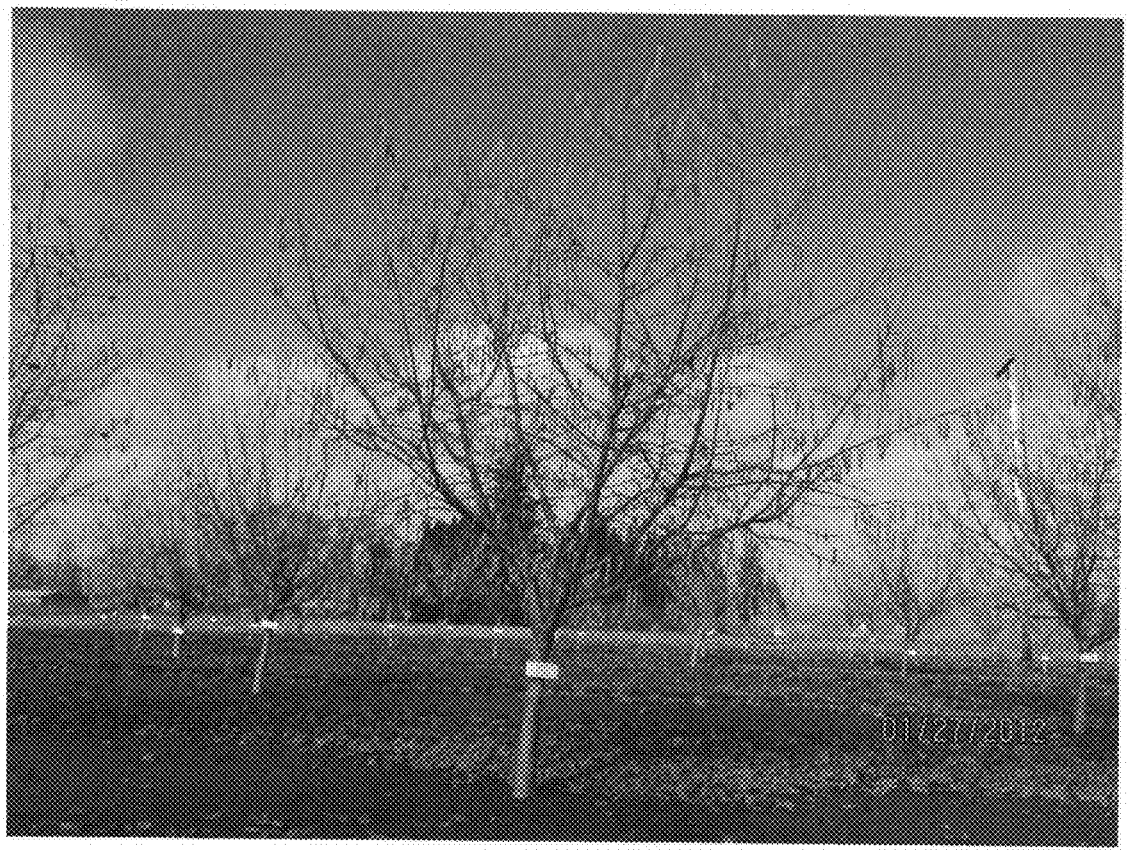
FIG. 2 shows a tree of the new cultivar 'McDonald' hazelnut in winter at end of 7th leaf.
Figure 3:
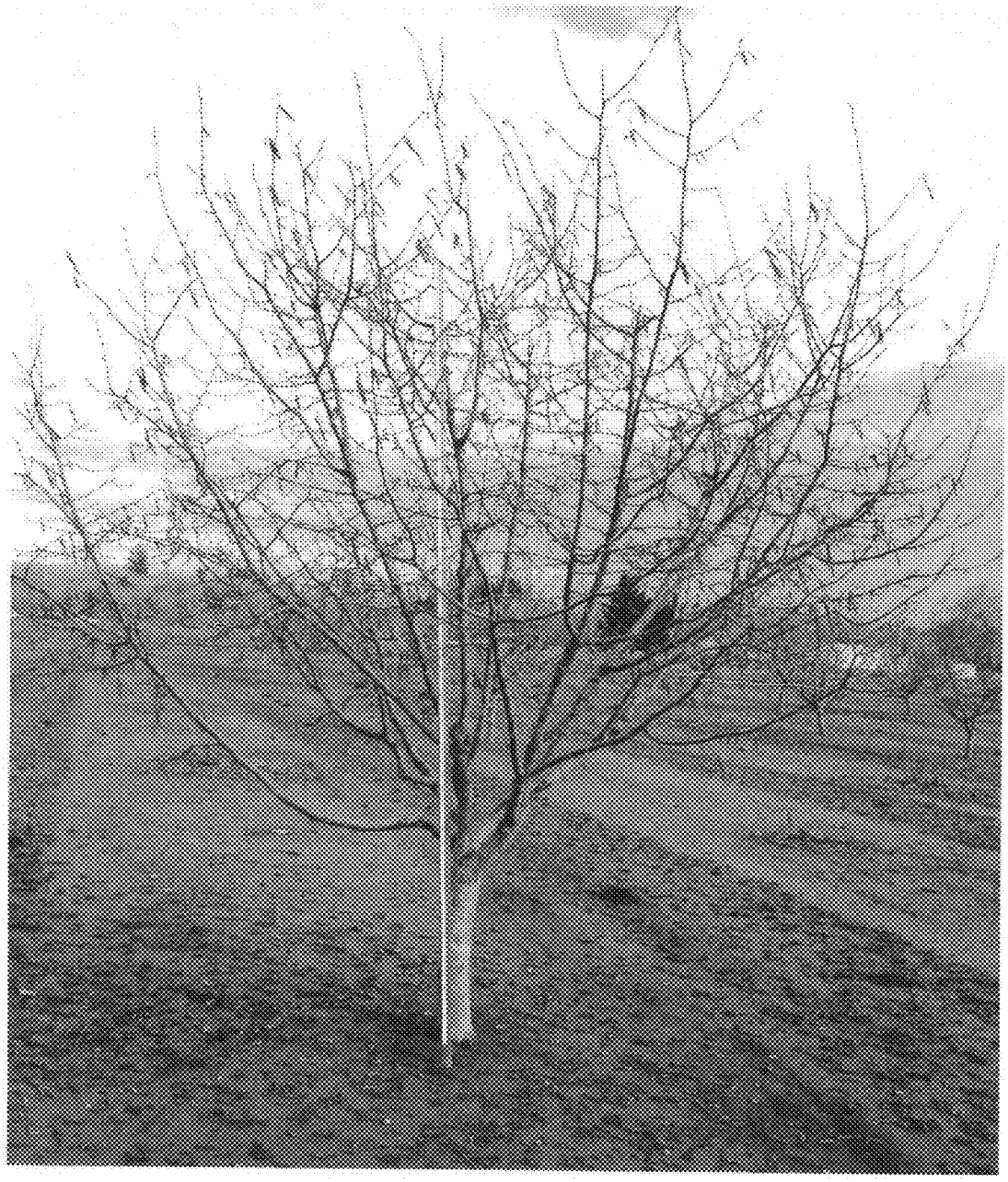
FIG. 3 shows a tree of the new cultivar 'McDonald' tree in winter at end of 7th leaf.
Figure 4:
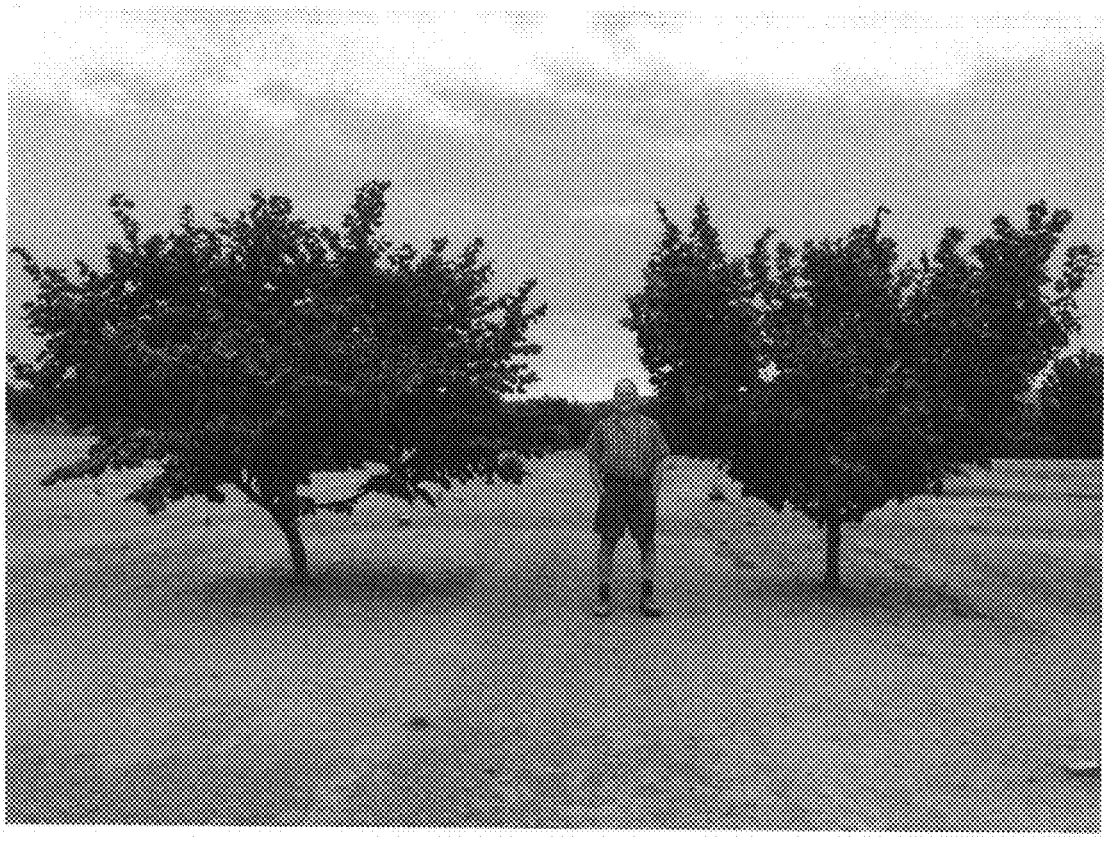
FIG. 4 shows August 2013 trees of the new cultivar 'McDonald' (left) and 'Jefferson' (right, unpatented), 8th leaf.
Figure 5:
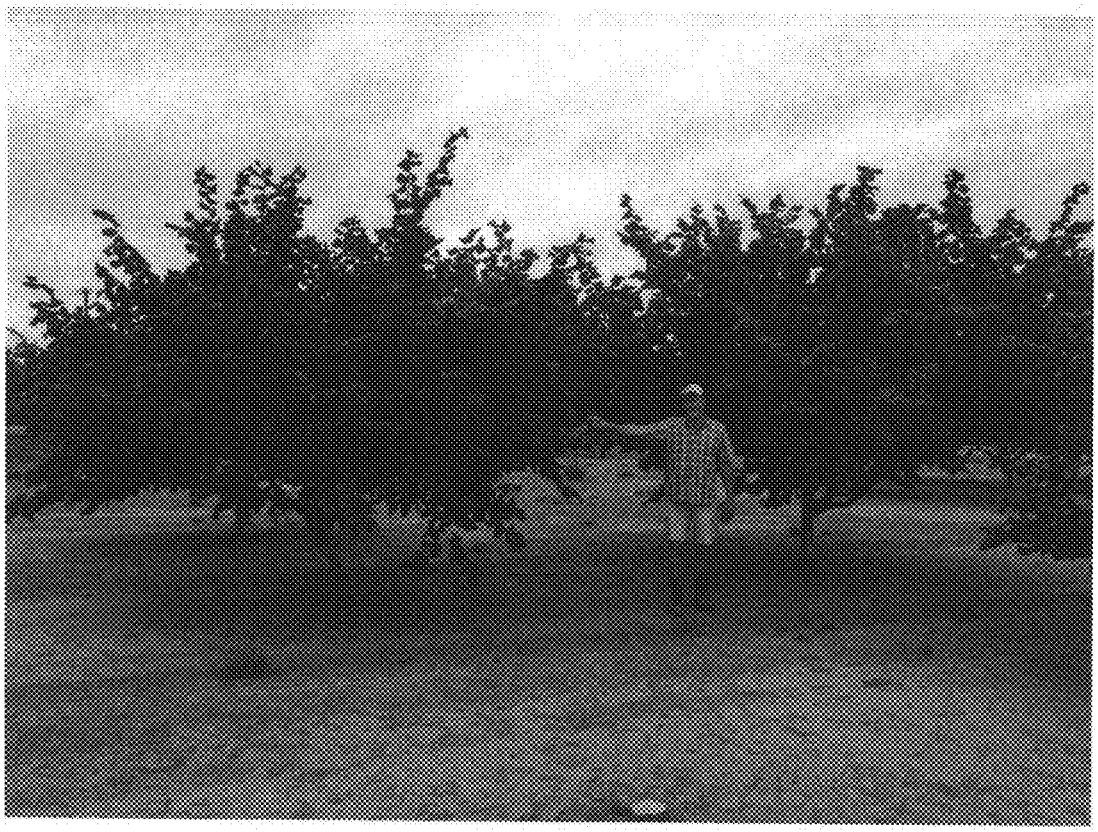
FIG. 5 shows trees of the new cultivar 'McDonald' (left) and 'Wepster' (right, unpatented), 8th leaf.
Figure 6:
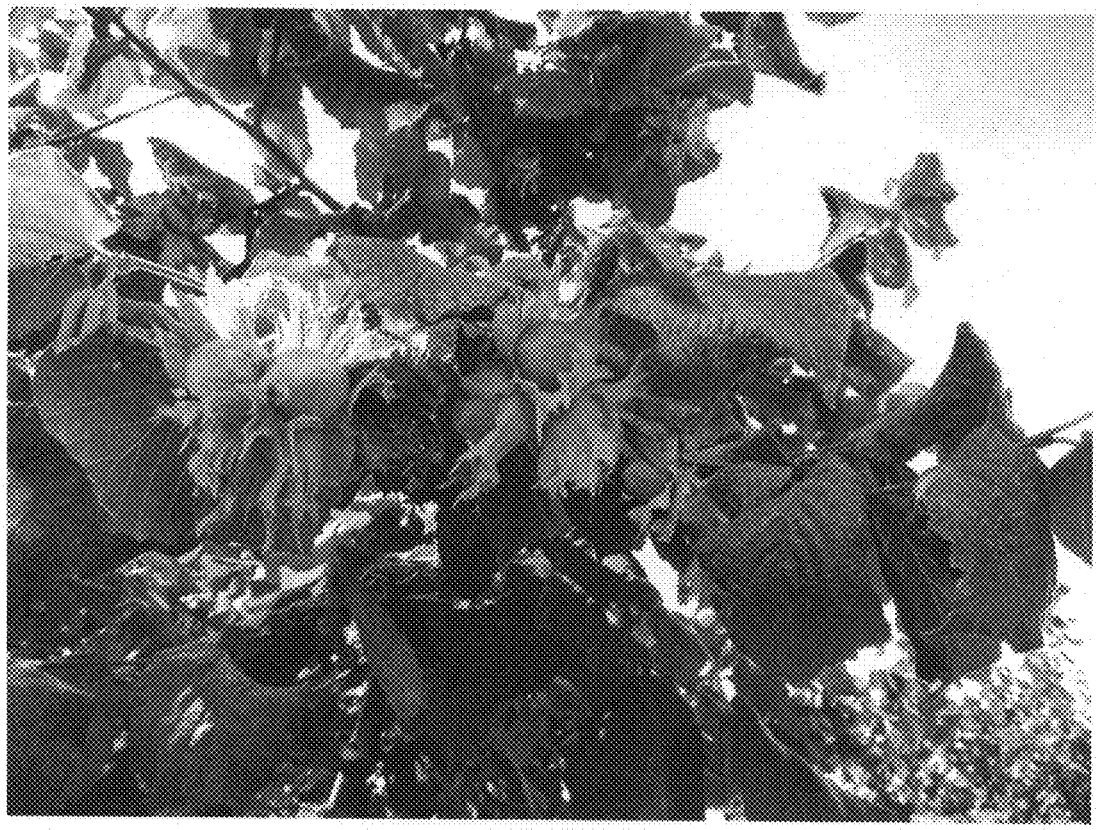
FIG. 6 shows nuts, husks and leaves of 'McDonald' hazelnut.
Figure 7:
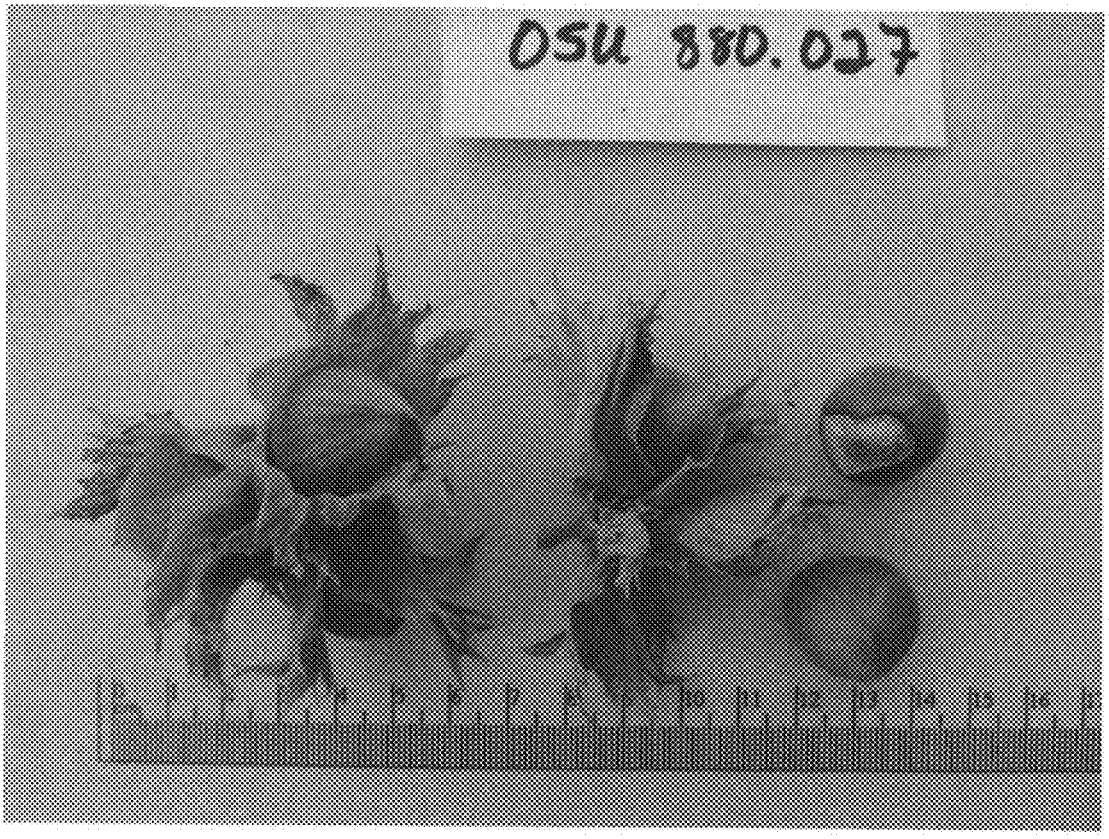
FIG. 7 shows nuts and husks of 'McDonald' hazelnut.
Figure 8:
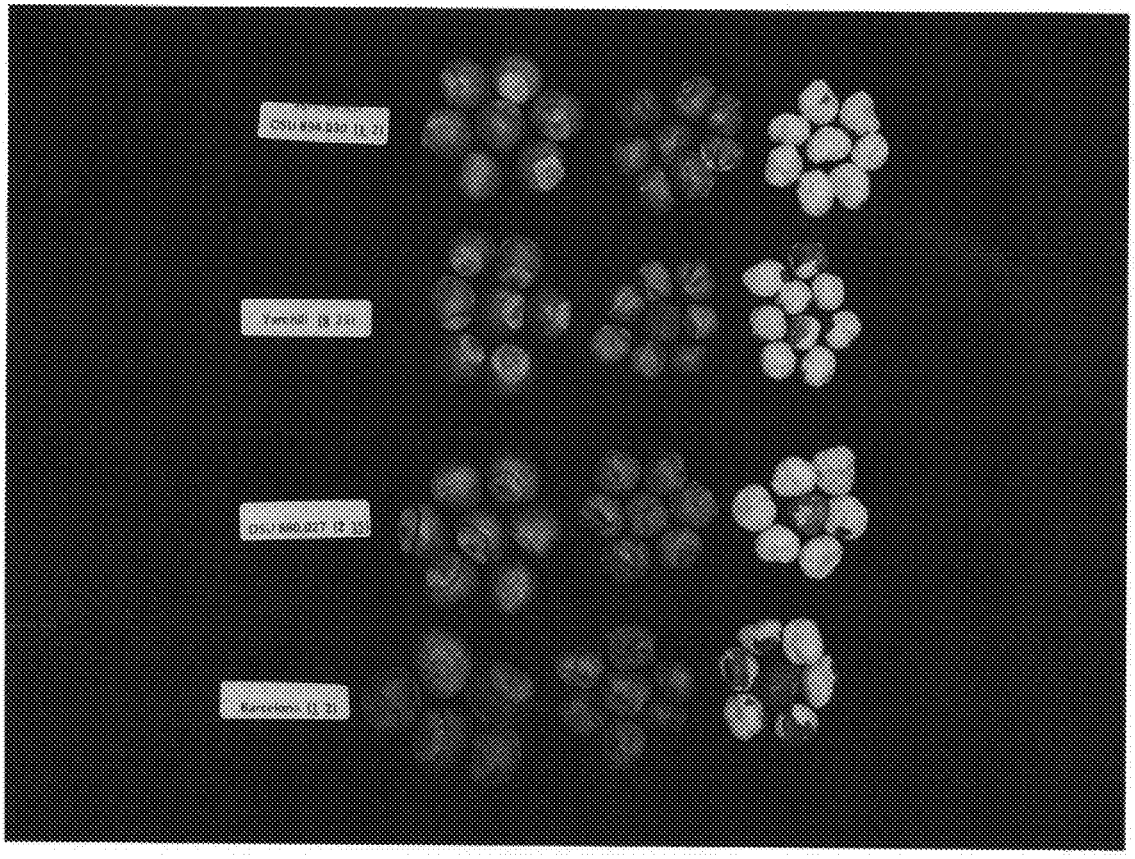
FIG. 8 shows nuts, raw kernels, and blanched kernels of hazelnuts 'Wepster' (OSU 894.030), 'Yamhill', 'McDonald' (OSU 880.027) and 'Barcelona'.
Figure 9:
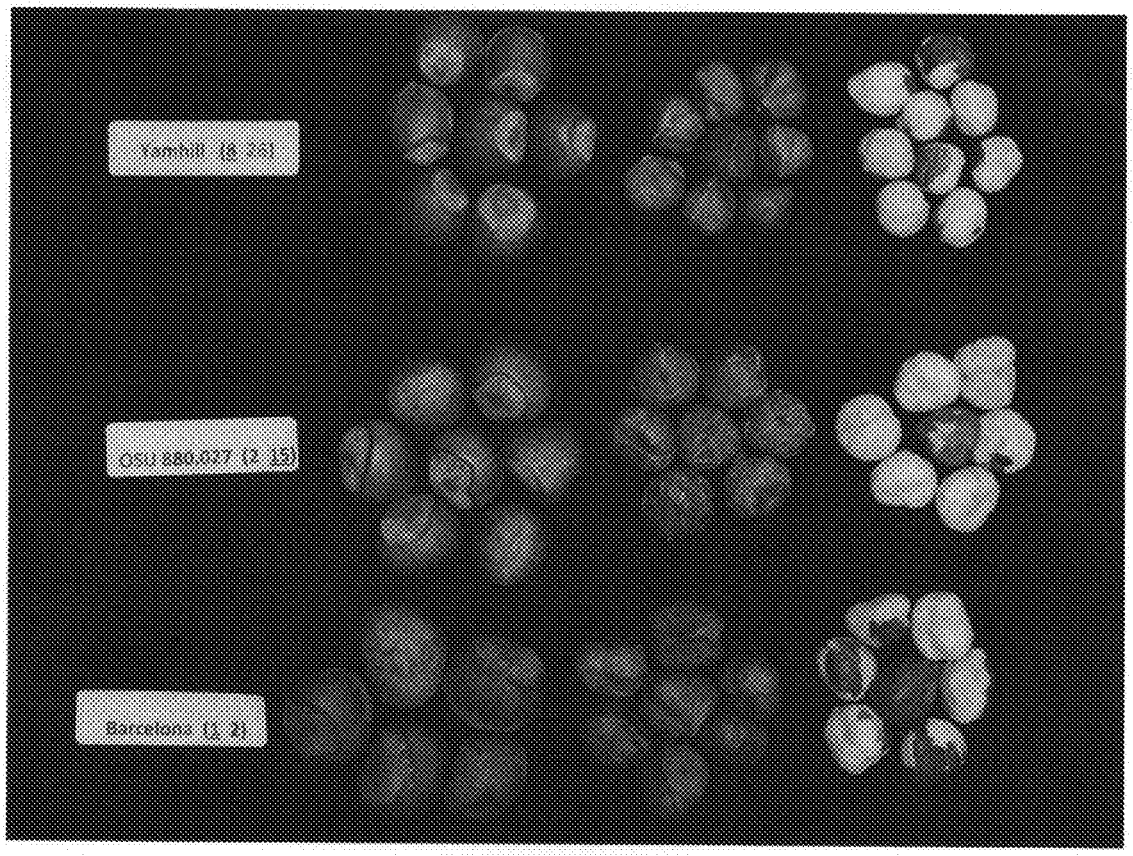
FIG. 9 shows nuts, raw kernels and blanched kernels of hazelnuts 'Yamhill', 'McDonald' (OSU 880.027) and 'Barcelona'.
Figure 10:
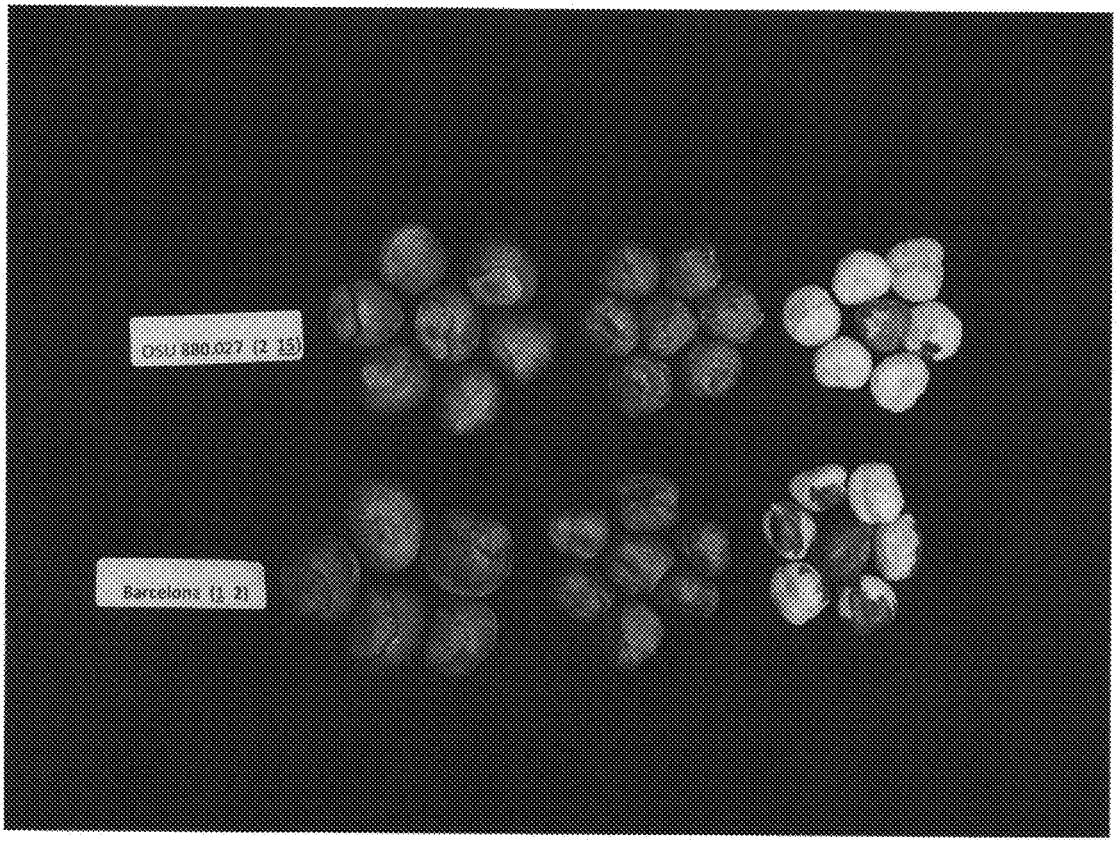
FIG. 10 shows nuts, raw kernels and blanched kernels of hazelnuts 'McDonald' (OSU 880.027) and 'Barcelona'.

The cultivar 'McDonald' has not been observed under all possible environmental conditions. The phenotype may vary somewhat with variations in environment such as temperature and light intensity, without, however, any variance in genotype. The aforementioned photographs and following observations and measurements describe plants grown in Corvallis, Oreg. under commercial practice outdoors in the field during the fall, winter and spring. Plants used for the photographs and description were propagated by tie-off layerage and growing on their own roots, and seven or eight years old. In the following description, color references are made to The Royal Horticultural Society Colour Chart, 1966 Edition, except where general terms of ordinary dictionary significance are used. The list of UPOV descriptors are from the Mar. 28, 1979 Hazelnut guidelines from UPOV.

Botanical classification: *Corylus avellana* cultivar 'McDonald'.

Parentage:

- *Female, or seed, parent.*—*Corylus avellana* cultivar 'Tonda Pacifica' (U.S. Plant Pat. No. 22,715). 'McDonald' is resistant to eastern filbert blight, while 'Tonda Pacifica' is highly susceptible. 'McDonald' and 'Tonda Pacifica' have different alleles at 16 of the 21 microsatellite markers loci. 'McDonald' has incompatibility alleles 2 and 15. 'Tonda Pacifica' and 'Wepster' have alleles 1 and 2. 'McDonald' has a shorter husk than 'Tonda Pacifica' and earlier nut maturity.
- *Male, or pollen, parent.*—*Corylus avellana* cultivar 'Santiam' (unpatented).

Propagation (type rooted suckers):

- *Time to initiate roots.*—About 30 days at 20° C.
- *Time to produce a rooted young plant.*—About six months at 22° C.
- *Root description.*—Fine to thick; freely branching; creamy white in color.

Propagation (type whip grafting):

- *Time to budbreak on the scions.*—About 14 days at 25° C.
- *Time to produce a grafted plant.*—About six months at 25° C.

Plant description:

- *General appearance.*—Natural habit is perennial shrub, but in commercial orchards, is a single trunk tree. Upright-spreading plant habit.
- *Growth and branching habit.*—Freely branching; about 15 lateral branches develop per plant. Pinching, that is, removal of the terminal apices, enhances branching with lateral branches potentially forming at every node.
- *Vigor.*—Moderate vigor growth habit.
- *Size.*—Plant height is about 5 meters; plant diameter or spread is about 5 meters.
- *Trunk.*—At 30 cm above the soil line, 10.52 cm in 2007.

Lateral branch description:

- *Length.*—About 33.5 cm.
- *Diameter.*—About 5 mm.
- *Internode length.*—About 3.2 cm.
- *Texture.*—Smooth, glabrous.
- *Strength.*—Strong. Color, immature: 139D.
- *Color, mature.*—177D.

Foliage description:

- *Arrangement.*—Alternate, simple.
- *Length.*—About 10.4 cm.
- *Width.*—About 8.7 cm.
- *Shape.*—Oblong to ovate.
- *Apex.*—Obtuse to acute.
- *Base.*—Cordate.
- *Margin.*—Serrate.
- *Texture, upper and lower surfaces.*—Slightly pubescent.
- *Venation pattern.*—Pinnate.
- *Color.*—Developing foliage, upper surface 141C, lower surfaces: 139C. Fully expanded foliage, upper surface: Spring and summer, 139B; late summer and fall, 139B. Fully expanded foliage, lower surface: Spring and summer, 139C; late summer and fall, 139C. Venation, upper surface: Spring and summer, 139C; late summer and fall, 139C. Venation, lower surface: Spring and summer, 139D; late summer and fall, 139D.

Leaf but description:

- *Shape.*—Globular.
- *Time of leaf budbreak.*—Descriptor=6 (medium to late). 'McDonald' leaf budbreak one week before 'Dorris', 'York' and 'Wepster'; 4 days later than 'Tonda Pacifica' and 'Sacajawea'.
- *Color.*—178C.

Petiole description:

- *Length.*—About 2.7 cm.
- *Diameter.*—About 1.8 mm.
- *Texture, upper and lower surfaces.*—Pubescent.
- *Color, upper surface.*—Spring and summer, 139D; late summer and fall, 139D.
- *Color, lower surface.*—Spring and summer, 139D; late summer and fall, 139D.

Flower description: Male inflorescences are catkins, color prior to elongation 176D. Catkin length 31.7 mm. Female inflorescence style color 047B.

- *Time of female flowering.*—Descriptor=5 (medium).
- *Time of female flowering compared to male flowering.*—Protogyny (descriptor=1, earlier).
- *Involucre constriction.*—Absent.
- *Involucre length.*—1.5 times length of nut, descriptor=5.
- *Size of indentation.*—Descriptor=7 (strong).

*Strength of serration of indentation*.—Descriptor=7 (strong).

*Pubescence on husk*.—Descriptor=9 (present).

*Thickness of callus at base*.—Descriptor=5 (medium).

*Jointing of bracts*.—Descriptor=2 (on one side).

Nut description:

*Length*.—About 18.4 mm.

*Width*.—About 18.9 mm.

*Depth*.—About 17.9 mm.

*Nut shape*.—Round. Nut shape index [(Width+Depth)/2*Length]=1.00. Nut compression index (Width/Depth)=1.05.

*Nut shell color*.—164A. Nut weight: About 2.51 grams.

*Kernel weight*.—About 1.29 grams.

*Kernel percentage* (*kernel weight/nut weight*).—About 51.5%.

*Number of fruits per cluster*.—Two to three.

*Nut shell coloration*.—164A.

*Number of stripes on shell*.—Descriptor=3 (few).

*Prominence of fruit apex*.—Medium prominent, descriptor=5.

*Size of fruit pistil scar on shell*.—Very small, descriptor=3.

*Hairiness of top of fruit*.—Weak, descriptor=3.

*Curvature of nut basal scar*.—Flat.

*Double kernels*.—Absent.

*Kernel shape*.—Globular.

*Shape of kernel in cross-section*.—Circular.

*Lateral groove in kernel*.—Absent.

*Corkiness of pellicle of kernel*.—Rating 2.6 (vs. 3.0 for 'Jefferson'); descriptor=4 (slight to medium corky).

*Nut yield* (*pounds per tree or per acre*).—Total 17.11 kg per tree in first trial, 21.43 kg per tree in second trial.

*Storability of fruits*.—Excellent, similar to OSU releases and check cultivars.

Disease/pest resistance: Plants of the new *Corylus* are highly resistant to eastern filbert blight caused by the fungus *Anisogramma anomala* (Peck) E. Müller, although a few small cankers may develop under high disease pressure. Plants of the new *Corylus* are resistant to bud mites (*Phytoptus avellanae* Nal.), while plants of 'Tonda Gentile delle Langhe' are highly susceptible, and plants of 'Barcelona' are highly resistant.

Temperature tolerance: Plants of the new *Corylus* have been observed to tolerate temperatures from −21 to 38° C. in the field in Corvallis, Oreg.

COMPARATIVE DATA

Tree size, growth habit, yield, and yield efficiency Tree sizes in the two trials were estimated by measuring trunk diameters 30 cm above the soil line, at the end of the $7^{th}$ growing season (December 2012 and 2013, respectively). Trunk cross-sectional area (TCA) was calculated from trunk diameter. Trees of 'McDonald' are moderately vigorous, and their upright-spreading growth habit should be grower-friendly (easy to manage).

In the first trial (Table 1), TCA of 'McDonald' (86.9 $cm^2$) was similar to 'Jefferson' (unpatented), 'Dorris', and 'York' (U.S. Plant Pat. No. 24,972). Trees were larger than 'Yamhill' (unpatented) but smaller than 'Wepster'. Total nut yield per tree was 17.11 kg, which is slightly less than 'Jefferson', 'Yamhill' and 'Wepster' and about the same as 'Dorris' and 'Sacajawea' (unpatented). Nut yield efficiency of 'McDonald' (0.198 $kg/cm^2$) was similar to 'Sacajawea' and 'Wepster', and lower than 'Jefferson' and 'Yamhill'.

In the second trial (Table 1), trees of 'McDonald' were similar in size to 'Jefferson'. In adjacent rows planted at the same time to EFB-susceptible selections, TCAs for 'Barcelona', 'Lewis' and 'Clark' were 138.6, 77.6 and 63.7 $cm^2$, respectively. The TCA of 'McDonald' is 63% of 'Barcelona'. In previous trials, tree size of 'Jefferson' and 'Lewis' has been about 70% of 'Barcelona'. Growers have been pleased with this level of vigor. Total nut yield per tree was 21.43 kg for 'McDonald' vs. 22.99 kg for 'Jefferson', 16.88 kg for the pollinizer 'Felix' (U.S. Plant Pat. No. 24,973), and 17.68 kg for 'Santiam'. Nut yield efficiency for 'McDonald'7 (0.245 $kg/cm^2$), which adjusts for differences in tree size, was similar to 'Santiam' (0.267 $kg/cm^2$), lower than 'Jefferson' (0.299 $kg/cm^2$) and higher than 'Felix' (0.133 $kg/cm^2$).

TABLE 1

Nut yield, trunk cross-sectional area, and yield efficiency of 'McDonald' and other hazelnut cultivars and selections in two trials

| Cultivar | No. trees | Yield per tree (kg) Year 3 | Year 4 | Year 5 | Year 6 |
|---|---|---|---|---|---|
| First trial (2006 planting) | | | | | |
| OSU 833.082 | 7 | 0.71 | 2.60 | 2.25 | 5.95 |
| OSU 879.031 | 7 | 0.31 | 1.42 | 2.13 | 5.17 |
| 'McDonald' | 7 | 0.29 | 1.13 | 2.44 | 6.54 |
| OSU 881.078 | 7 | 0.23 | 1.08 | 2.08 | 5.08 |
| Dorris | 7 | 0.42 | 2.84 | 3.30 | 6.51 |
| Jefferson | 7 | 0.41 | 3.55 | 3.35 | 6.97 |
| Sacajawea | 7 | 0.26 | 1.92 | 2.51 | 6.52 |
| Santiam | 7 | 0.29 | 1.76 | 3.73 | 7.25 |
| Wepster | 7 | 0.24 | 1.56 | 2.56 | 6.62 |
| Yamhill | 7 | 0.78 | 2.79 | 3.88 | 7.34 |
| York | 7 | 0.41 | 1.52 | 2.48 | 6.13 |
| $LSD_{0.05}$ | | 0.17 | 0.55 | 0.75 | 0.89 |
| Second trial (2007 planting) | | | | | |
| 'McDonald' | 4 | 0.15 | 1.10 | 4.85 | 7.38 |
| Felix | 4 | 0.06 | 1.04 | 2.91 | 7.93 |
| Jefferson | 4 | 0.55 | 1.97 | 5.63 | 4.60 |
| Santiam | 4 | 0.20 | 1.11 | 4.09 | 5.46 |
| $LSD_{0.05}$ | | 0.21 | 0.43 | 0.54 | 2.04 |

| Cultivar | No. trees | Yield per tree (kg) Year 7 | Total | $TCA^z$ ($cm^2$) | $YE^y$ ($kg \cdot cm^{-2}$) |
|---|---|---|---|---|---|
| First trial (2006 planting) | | | | | |
| OSU 833.082 | 7 | 2.46 | 13.97 | 68.1 | 0.205 |
| OSU 879.031 | 7 | 6.54 | 15.58 | 87.2 | 0.179 |
| 'McDonald' | 7 | 6.71 | 17.11 | 86.9 | 0.198 |
| OSU 881.078 | 7 | 6.67 | 15.15 | 112.4 | 0.135 |
| Dorris | 7 | 5.70 | 18.78 | 84.0 | 0.225 |
| Jefferson | 7 | 5.79 | 20.07 | 85.4 | 0.235 |
| Sacajawea | 7 | 6.76 | 17.97 | 93.7 | 0.196 |
| Santiam | 7 | 6.34 | 19.36 | 79.2 | 0.244 |
| Wepster | 7 | 8.68 | 19.67 | 99.2 | 0.198 |
| Yamhill | 7 | 4.94 | 19.73 | 78.5 | 0.249 |
| York | 7 | 4.42 | 14.97 | 85.6 | 0.175 |
| $LSD_{0.05}$ | | 1.26 | 2.62 | 10.4 | 0.027 |
| Second trial (2007 planting) | | | | | |
| 'McDonald' | 4 | 7.95 | 21.43 | 87.55 | 0.245 |
| Felix | 4 | 4.95 | 16.88 | 128.43 | 0.133 |
| Jefferson | 4 | 10.25 | 22.99 | 77.52 | 0.299 |

TABLE 1-continued

Nut yield, trunk cross-sectional area, and yield efficiency of 'McDonald' and other hazelnut cultivars and selections in two trials

| | | | | | |
|---|---|---|---|---|---|
| Santiam | 4 | 6.83 | 17.68 | 66.81 | 0.267 |
| $LSD_{0.05}$ | | 1.18 | 2.45 | 13.48 | 0.029 |

[z]Trunk cross-sectional area calculated from trunk diameters measured in late fall at the end of the seventh season.
[y]Yield efficiency = Total nut yield/TCA.

A high percentage of the nuts and kernels of 'McDonald' in both trials were marketable (Table 2). Very few moldy kernels were observed in 'McDonald', in striking contrast to 'Santiam'.

TABLE 2

Frequency of good nuts, and of nut and kernel defects in 'McDonald; and other hazelnut cultivars and selections in trials planted in 2006 and 2007

| | Frequency (%)[z] | | | |
|---|---|---|---|---|
| Selection | Good | Blanks | Brown stain | Moldy |
| First trial (n = 7) | | | | |
| OSU 879.031 | 92.7 | 3.7 | 0.4 | 1.0 |
| 'McDonald' | 88.0 | 2.7 | 0.0 | 1.0 |
| OSU 881.078 | 84.7 | 8.9 | 0.0 | 2.1 |
| OSU 833.082 | 87.0 | 4.4 | 0.0 | 4.0 |
| Dorris | 80.7 | 7.5 | 0.2 | 4.2 |
| Jefferson | 84.2 | 3.8 | 0.1 | 4.4 |
| Sacajawea | 87.8 | 3.1 | 0.0 | 3.4 |
| Wepster | 86.7 | 7.6 | 0.2 | 1.1 |
| Yamhill | 91.3 | 2.3 | 0.1 | 2.2 |
| York | 83.7 | 8.7 | 0.3 | 1.7 |
| Santiam | 76.2 | 3.0 | 0.0 | 7.9 |
| $LSD_{0.05}$ | 5.6 | 3.6 | 0.9 | 2.2 |
| Second trial (n = 4) | | | | |
| 'McDonald' | 83.5 | 5.1 | 0.1 | 2.1 |
| Felix | 88.9 | 4.2 | 0.2 | 2.1 |
| Jefferson | 80.1 | 4.3 | 0.3 | 5.7 |
| Santiam | 68.8 | 2.8 | 0.1 | 17.3 |
| $LSD_{0.05}$ | 3.5 | 2.5 | 0.3 | 2.3 |

| | Frequency (%)[z] | | | |
|---|---|---|---|---|
| Selection | Shrivel | Poor fill | Twins | Black tips |
| First trial (n = 7) | | | | |
| OSU 879.031 | 1.0 | 0.6 | 0.3 | 0.3 |
| 'McDonald' | 7.5 | 0.5 | 0.0 | 0.3 |
| OSU 881.078 | 2.8 | 1.1 | 0.1 | 0.3 |
| OSU 833.082 | 2.8 | 0.7 | 0.5 | 0.6 |
| Dorris | 4.3 | 1.9 | 0.1 | 1.2 |
| Jefferson | 2.8 | 3.8 | 0.5 | 0.5 |
| Sacajawea | 3.1 | 1.2 | 0.1 | 1.3 |
| Wepster | 2.7 | 1.4 | 0.1 | 0.3 |
| Yamhill | 2.5 | 1.6 | 0.0 | 0.1 |
| York | 2.8 | 1.2 | 0.0 | 1.6 |
| Santiam | 9.4 | 2.3 | 0.2 | 0.9 |
| $LSD_{0.05}$ | 2.7 | 2.3 | 0.5 | 0.9 |
| Second trial (n = 4) | | | | |
| 'McDonald' | 4.5 | 4.5 | 0.1 | 0.3 |
| Felix | 0.4 | 2.9 | 0.3 | 1.1 |
| Jefferson | 0.4 | 8.9 | 0.6 | 0.6 |
| Santiam | 1.8 | 9.6 | 0.1 | 0.1 |
| $LSD_{0.05}$ | 1.0 | 2.5 | 0.4 | 0.5 |

[z]Means of years 4-7.
LSD = least significant difference.

Percent kernel (the ratio of kernel weight to nut weight) for 'McDonald' (52%) is higher than 'Barcelona' (typically 43%) and 'Jefferson' (45%) (Table 3). Yields of kernels per acre would be high for 'McDonald'. Although 'McDonald' is not the highest-yielding selection, its yields have been consistently good and the nuts consistently well-filled. In contrast, 'Yamhill' trees occasionally set very heavy nut crops, and the nuts can be so poorly filled that the kernels are not marketable.

TABLE 3

Nut and kernel weight, kernel percentage, and ratings for fiber, blanching and bud mite susceptibility for 'McDonald'and other hazelnut cultivars and selections in two trials.

| Selection | Nut wt (g)[z] | Kernel wt (g) | Kernel percentage | Fiber[y] | Blanch-ing[x] | Bud mite[w] |
|---|---|---|---|---|---|---|
| First trial (n = 7) | | | | | | |
| OSU 879.031 | 2.34 | 1.15 | 49.0 | — | 5.2 | — |
| McDonald' | 2.39 | 1.21 | 50.7 | — | 3.8 | — |
| OSU 881.078 | 2.37 | 0.97 | 41.0 | — | 4.5 | — |
| OSU 833.082 | 2.72 | 1.12 | 41.3 | — | 2.6 | — |
| Dorris | 3.24 | 1.32 | 40.8 | — | 2.9 | — |
| Jefferson | 3.53 | 1.51 | 42.8 | — | 4.8 | — |
| Sacajawea | 2.52 | 1.29 | 51.2 | — | 2.8 | — |
| Santiam | 2.09 | 1.03 | 49.5 | — | 5.1 | — |
| Wepster | 2.23 | 0.98 | 43.9 | — | 3.1 | — |
| Yamhill | 2.18 | 1.01 | 46.4 | — | 5.0 | — |
| York | 2.59 | 1.12 | 43.4 | — | 4.8 | — |
| $LSD_{0.05}$ | 0.23 | 0.13 | 3.0 | — | 0.7 | — |
| Second trial (n = 4) | | | | | | |
| 'McDonald' | 2.62 | 1.37 | 52.3 | 2.6 | 3.3 | 1.8 |
| Felix | 2.71 | 1.37 | 50.8 | 3.0 | 2.2 | 2.0 |
| Jefferson | 3.76 | 1.67 | 44.5 | 3.0 | 4.3 | 1.2 |
| Santiam | 2.28 | 1.15 | 50.6 | 3.0 | 4.2 | 2.2 |
| $LSD_{0.05}$ | 0.22 | 0.04 | 1.0 | 0.1 | 0.4 | 0.2 |

[z]Means for nuts and kernels are over four years.
[y]Amount of fiber on the pellicle was rated in the second trial from 1 (none) to 4 (much).
[x]Blanching was rated from 1 (complete pellicle removal) to 7 (no pellicle removal).
[w]Susceptibility to bud mite (primarily *Phytoptus avellanae* Nal.) was rated on four trees of each selection in the second trial on a scale of 1 (no blasted buds) to 5 (many blasted buds). Shown are mean ratings for 5 years (2009-2013).
LSD = least significant difference.

Figure 11:
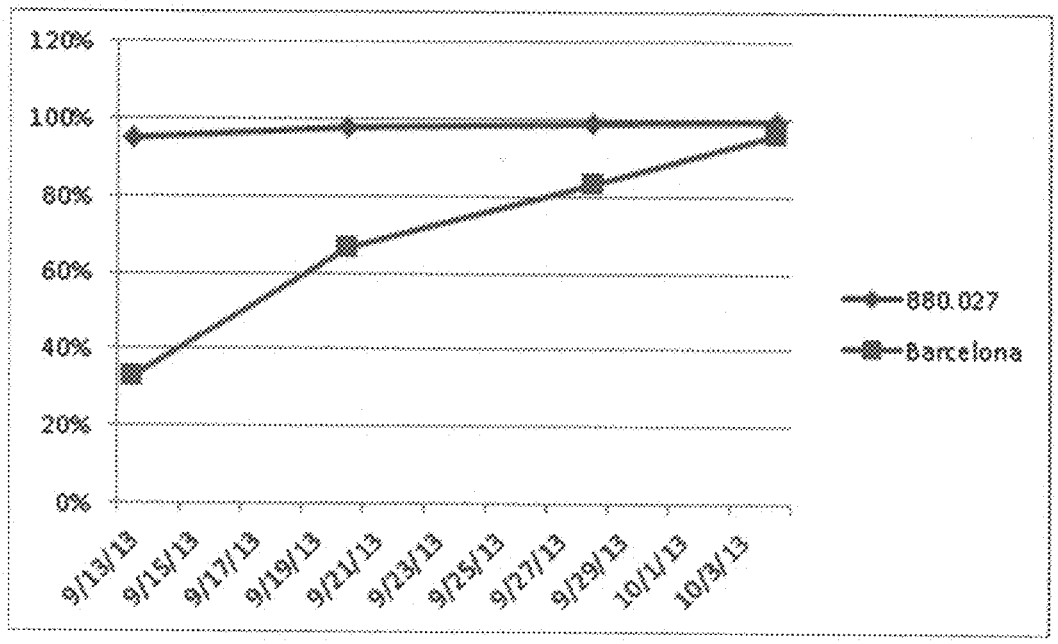
FIG. 11 is a graph showing maturity of 'McDonald' (OSU 880.027) and 'Barcelona' based on percentage of nuts on the ground. Four trees of each genotype were harvested in 2013 on four dates (September 13, September 20, September 27 and October 4). Percentages of nuts on the ground based on weight are cumulative.
Figure 13C:
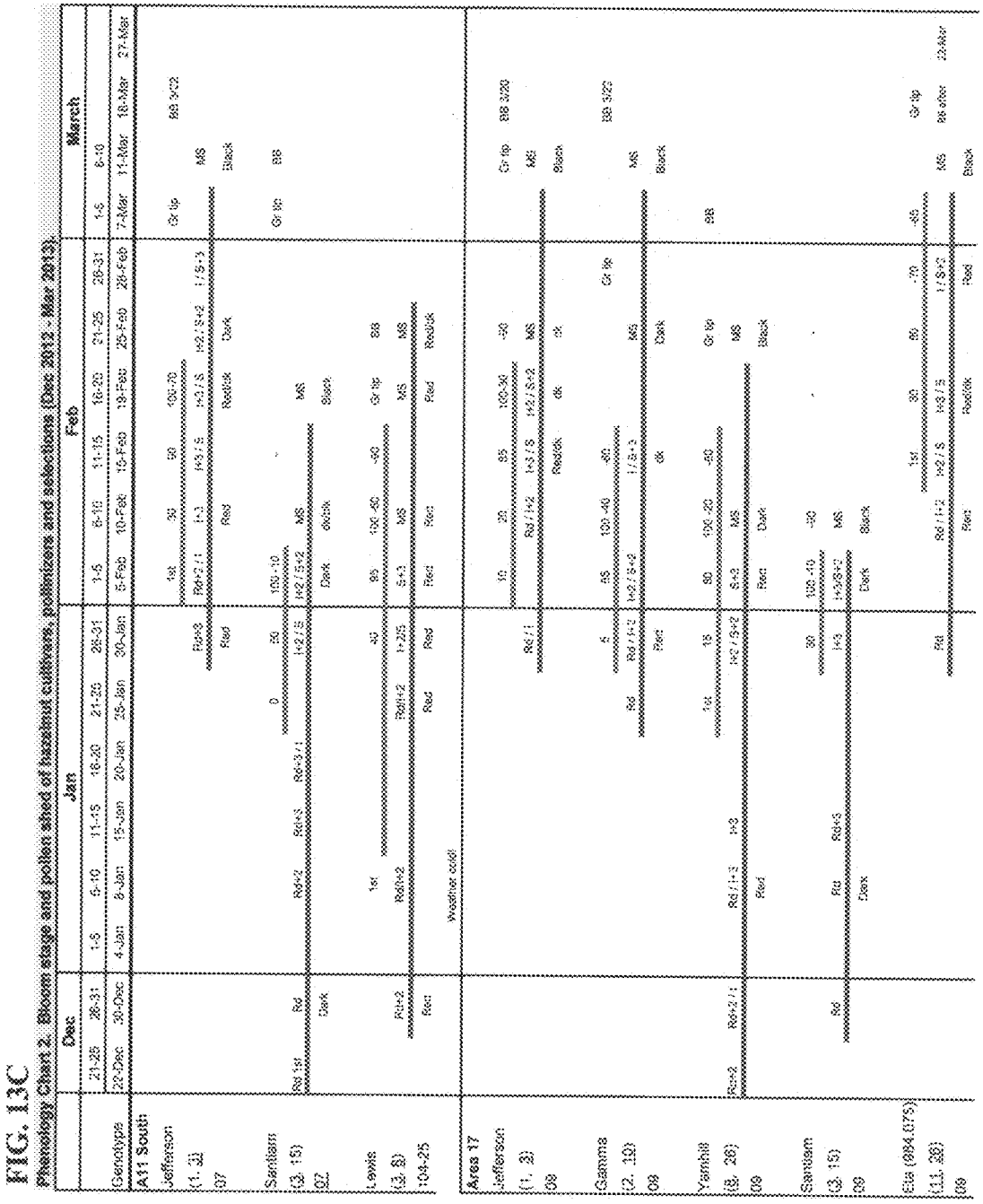
Figure 13D:
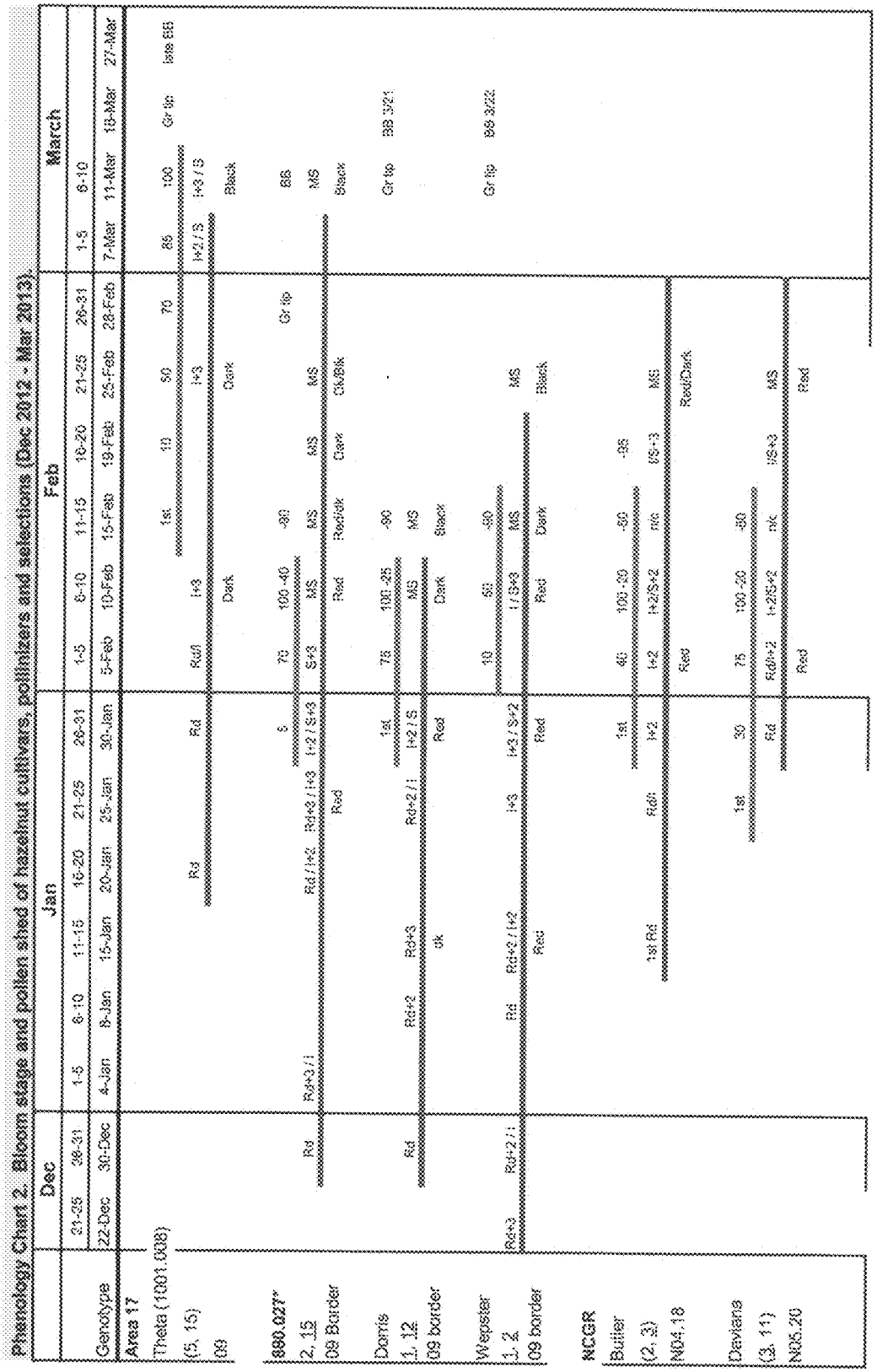

Nut maturity date. The nuts of 'McDonald' are borne in clusters of 2-3 in husks about 50% longer than the nuts. The husks are slit down the side, and flare open as they dry at maturity. About 95% of the nuts fall free of the husk at maturity (range 85-100%). The other 5% of the nuts would come out of the husks as they moved through the harvester. When mature, the shells are light tan in color. Harvest date is estimated to be 14 days before 'Barcelona', allowing it to be harvested before the start of the rainy season (Table 4 and FIG. 11).

TABLE 4

Harvest notes for four hazelnut genotypes harvested by hand for three years in the second trial.

| Year | Selection | Date | Down[z] | Free[y] |
|---|---|---|---|---|
| 2010 | 'McDonald' | Sep. 28 | 88 | 99 |
| | Felix | Oct. 12 | 87 | 77 |
| | Jefferson | Oct. 12 | 86 | 78 |
| | Santiam | Sep. 28 | 89 | 97 |
| 2011 | 'McDonald' | Oct. 27 | 96 | 93 |
| | Felix | Oct. 27 | 96 | 81 |
| | Jefferson | Oct. 27 | 88 | 64 |
| | Santiam | Sep. 30 | 81 | 94 |
| 2012 | 'McDonald' | Oct. 4 | 97 | 98 |
| | Felix | Oct. 18 | 85 | 84 |

TABLE 4-continued

Harvest notes for four hazelnut genotypes harvested by hand for three years in the second trial.

| Year | Selection | Date | Down[z] | Free[y] |
|---|---|---|---|---|
| | Jefferson | Oct. 18 | 81 | 89 |
| | Santiam | Oct. 5 | 97 | 91 |

[z]Estimated percentage of nuts on the ground as opposed to in the tree.
[y]Of the nuts on the ground, estimated percentage free of the husk.

Nuts in the first trial were annually raked and fed through a Mave harvester. Nuts in the second trial were hand-harvested and notes recorded at the time of harvest (Table 4). Notes included the date, the percentage of nuts on the ground (as opposed to in the tree), and the percentage of the nuts on the ground that were free of the husk (as opposed to inside the husk). We harvest more than 2000 trees by hand every fall, visiting a block once every 7 to 10 days, and harvesting a tree if >70% of the nuts are on the ground. Thus the percentages are estimates. The harvest dates and percentage down indicate that maturity of 'McDonald' is about 14 days earlier than 'Barcelona' (Table 4). To more precisely estimate nut maturity, the four trees of 'McDonald' in the second trial and four trees of 'Barcelona' in adjacent rows were harvested by hand at weekly intervals in the final year of the trial (2013). The maturity curves from the 2013 harvest (FIG. 11) show that nuts of 'McDonald' drop at least 14 days sooner than those of 'Barcelona'. Most orchards planted since 2009 have been of 'Jefferson', which matures about three days after 'Barcelona'. Plantings of 'McDonald' and 'Wepster' would allow harvest to begin two weeks earlier.

Nut and kernel characteristics: 'McDonald' can be used in the blanched kernel market as a companion for 'Wepster' and an alternative to 'Yamhill', 'Lewis', 'Clark' and 'Sacajawea'. 'McDonald', like 'Wepster' and 'Yamhill', has a very high level of EFB resistance, while 'Lewis', 'Clark' and 'Sacajawea' have lower level of quantitative resistance. The nut shape is round with a slight point, which lends itself well to sizing and cracking. The shells are thin and easy to crack, and most kernels remain whole when the shell is broken. The kernel size of 'McDonald' is small, similar to 'Clark', and larger than 'Wepster'. Raw kernels are attractive and have a light brown pellicle with a moderate amount of attached fiber (rating =2.6) on a scale of 1 (no fiber) to 4 (much fiber). Pellicle removal is rated on a scale of 1 (complete pellicle removal) to 7 (no pellicle removal), with ratings <4.0 being desired. Most of the pellicle on 'McDonald' kernels is removed from the kernels with dry heat in the blanching process (ratings=3.8 and 3.3 in the first and second trials, respectively) which is better than 'Yamhill' (rating=5.0). Kernel texture, flavor and aroma are excellent, and desirable for use in baked goods and chocolate products.

In two trials, 'McDonald' produced fewer nut and kernel defects (and more good kernels) than 'Barcelona' in adjacent rows. The nut and kernel data were similar in the two trials. The frequency of moldy kernels in 'McDonald' in the two trials was very low (1.0-2.1%) in contrast to 'Jefferson' (4.4-5.7%) and especially 'Santiam' (7.89-17.3%). Kernel mold is a problem in 'Lewis' and 'Santiam', particularly when weather is cool and wet in spring and early summer. The frequency of poorly filled nuts is low compared to other selections, even though 'McDonald' crops consistently well.

Incompatibility and pollinizers. The trees set a moderate to high amount of catkins that shed copious amounts of pollen in early mid-season, with 'Wepster', 'York' and 'Yamhill'. Pollen has been collected and used in several controlled pollinations, and both quantity and viability appear to be very good. 'McDonald' has incompatibility alleles $S_2$ and $S_{15}$ as determined by fluorescence microscopy. Both alleles are expressed in the females, but only $S_{15}$ is expressed in the pollen because of dominance. By convention, alleles expressed in the pollen are underlined.

Time of pollen shed and female receptivity were recorded weekly from early December 2011 to late March 2013 (FIGS. 12A-12B). Female inflorescences of 'McDonald' emerged in early mid-season and were fully receptive in mid-January. 'Wepster' ($S_{\underline{1}}$ $S_2$) is recommended as a companion cultivar, as 'Wepster' and 'McDonald' are cross-compatible in both directions. At least one additional pollinizer that sheds compatible pollen in midseason and late-midseason is recommended. Suitable pollinizers include 'York' ($S_2$ $S_{\underline{21}}$) and 'Gamma' ($S_2$ $S_{\underline{10}}$). 'Yamhill' ($S_{\underline{8}}$ $S_{26}$) is also a suitable pollinizer and is an attractive option as "temporary trees" in double-density plantings. Pollen of 'Jefferson' ($S_1$ $S_{\underline{3}}$) is compatible on females of OSU 880.027, but the time of pollen shed is later than ideal. Pollen of 'Dorris' ($S_{\underline{1}}$ $S_{\underline{12}}$), 'Sacajawea' ($S_{\underline{1}}$ $S_{22}$) and 'Barcelona' ($S_{\underline{1}}$ $S_2$) is also compatible on females of OSU 880.027. Pollen of 'Tonda di Giffoni' ($S_{\underline{2}}$ $S_{23}$) is incompatible because it expresses $S_2$. Pollen of 'Delta' ($S_{\underline{1}}$ $S_{\underline{15}}$), 'Felix' ($S_{\underline{15}}$ $S_{\underline{21}}$) and 'Theta' ($S_{\underline{5}}$ $S_{\underline{15}}$) is incompatible because of the shared allele $S_{15}$. Inclusion of 'Wepster' as a companion cultivar in the orchard results in no loss in total nut yield. Alternative orchard designs include plantings of different cross-compatible cultivars in adjacent rows. Flowering times will continue to be observed, and pollinizer recommendations adjusted accordingly. Pollinizers with a high level of EFB resistance would eliminate the need for fungicide control in the entire orchard.

Pests and diseases. Based on DNA marker data, 'McDonald', like 'Wepster' and 'Yamhill', has a very high level of resistance to EFB conferred by a dominant allele from 'Gasaway', so fungicide applications are not needed. RAPD markers 152-800 and 268-580 that flank the resistance allele in 'Gasaway' are present in 'McDonald', and these markers are transmitted to its seedlings. Additional RAPD markers linked to resistance are also present. Trees of 'McDonald' have not yet been challenged with the EFB pathogen in glasshouse or structure inoculations. No cankers have been observed on the 11 trees of 'McDonald' in the yield trials, while several cankers have been noted on adjacent trees of susceptible genotypes.

Susceptibility to bacterial blight caused by *Xanthomonas campestris* pv. *corylina* has not been quantified, but no trees in the two trials were affected.

Susceptibility to big bud mite (primarily *Phytoptus avellanae* Nal.) was rated in the second trial (Table 3) after leaf fall once per year for five years (December 2009-2013). The scale was from 1 (no blasted buds) to 5 (many blasted buds). The average ratings indicate adequate resistance for 'McDonald' (1.8), 'Jefferson' (1.2), 'Felix' (2.0) and 'Santiam' (2.2). Blasted buds are very rare on 'McDonald', so chemical applications should not be necessary to control bud mite.

Propagation: Layers of 'McDonald' are moderately vigorous and root well, but have lower vigor and caliper than those of 'Jefferson' and 'Barcelona'.

DNA Fingerprinting: Primers used are shown in Table 5, and results shown in Table 6.

TABLE 5

Primers and annealing temperatures for the 21 microsatellite marker loci used to fingerprint 'McDonald' and other hazelnut cultivars.

| Locus | Repeat motif | Size | Primers 5'-3' (Forward above, Reverse below) | $T_s$ | n | He | Ho | PIC | r | LG | Reference | Locus |
|---|---|---|---|---|---|---|---|---|---|---|---|---|
| A614 | $(TC)_{17}(CA)_{10}NNN(CA)_6$ | 125-156 | Hex-TGGCAGAGCTTTGTCAGCTT (SEQ ID NO: 1) R-GCAGTGGAGGATTGCTGACT (SEQ ID NO: 2) | 60 | 14 | 0.85 | 0.85 | 0.84 | 0.00 | 6 | Gurcan et al. 2010a | A999614 |
| A616 | $(AC)_{11}$ | 136-162 | Fam-CACTCATACCGCAAACTCCA (SEQ ID NO: 3) R-ATGGCTTTTGCTTCGTTTTG (SEQ ID NO: 4) | 60 | 13 | 0.85 | 0.85 | 0.83 | 0.00 | 8 | Gurcan et al. 2010a | A616 |
| A640 | $(CT)_{15}(CA)_{13}$ | 354-378 | F-TGCCTCTGCAGTTAGTCATCAAATGTAGG (SEQ ID NO: 5) Fam-CGCCATATAATTGGGATGCTTGTTG (SEQ ID NO: 6) | 67 | 11 | 0.80 | 0.73 | 0.77 | 0.04 | 10 | Gurcan et al. 2010a | A640 |
| B619 | $(TC)_{21}$ | 146-180 | Fam-AGTCGGCTCCCCTTTTCTC (SEQ ID NO: 7) R-GCGATCTGACCTCATTTTTG (SEQ ID NO: 8) | 60 | 14 | 0.88 | 0.88 | 0.87 | 0.00 | 3 | Gurcan et al. 2010a | B619 |
| B634 | $(AG)_{15}$ | 218-238 | Hex-CCTGCATCCAGGACTCATTA (SEQ ID NO: 9) R-GTGCAGAGGTTGCACTCAAA (SEQ ID NO: 10) | 60 | 9 | 0.76 | 0.76 | 0.73 | 0.00 | 4 | Gurcan et al. 2010a | B634 |
| B671 | $(AG)_6NN(GA)_{17}$ | 221-249 | Hex-TTGCCAGTGCATACTCTGATG (SEQ ID NO: 11) R-ACCAGCTCTGGGCTTAACAC (SEQ ID NO: 12) | 60 | 13 | 0.86 | 0.88 | 0.84 | −0.01 | 9 | Gurcan et al. 2010a | B671 |
| B709 | $(GA)_{21}$ | 219-233 | Ned-CCAAGCACGAATGAACTCAA (SEQ ID NO: 13) R-GCGGGTTCTCGTTGTACACT (SEQ ID NO: 14) | 60 | 8 | 0.74 | 0.76 | 0.70 | 0.01 | 5 | Gurcan et al. 2010a | B709 |
| B733 | $(TC)_{15}$ | 161-183 | Ned-CACCCTCTTCACCACCTCAT (SEQ ID NO: 15) R-CATCCCCTGTTGGAGTTTTC (SEQ ID NO: 16) | 60 | 8 | 0.68 | 0.68 | 0.63 | 0.00 | 7.2 | Gurcan et al. 2010a | B733 |
| B741 | $(GT)_5(GA)_{12}$ | 176-194 | Fam-GTTCACAGGCTGTTGGGTTT (SEQ ID NO: 17) R-CGTGTTGCTCATGTGTTGTG (SEQ ID NO: 18) | 60 | 10 | 0.77 | 0.78 | 0.74 | 0.00 | 5 | Gurcan et al. 2010a | B741 |
| B749 | $(TC)_{12}$ | 200-210 | Hex-GGCTGACAACACAGCAGAAA (SEQ ID NO: 19) R-TCGGCTAGGGTTAGGGTTTT (SEQ ID NO: 20) | 60 | 6 | 0.60 | 0.64 | 0.51 | −0.03 | 1 | Gurcan et al. 2010a | B749 |

TABLE 5-continued

Primers and annealing temperatures for the 21 microsatellite marker loci used to fingerprint 'McDonald' and other hazelnut cultivars.

| Locus | Repeat motif | Size | Primers 5'-3' (Forward above, Reverse below) | $T_s$ | n | He | Ho | PIC | r | LG | Reference | Locus |
|---|---|---|---|---|---|---|---|---|---|---|---|---|
| B767 | $(TC)_{15}(AT)_7$ | 198-238 | Fam-CCACCAACTGTTTCACACCA (SEQ ID NO: 21) R-GCGAAATGGAGCTCTTGAAC (SEQ ID NO: 22) | 60 | 16 | 0.87 | 0.80 | 0.86 | 0.04 | 8 | Gurcan et al. 2010a | B767 |
| B774 | $(AG)_{15}$ | 195-213 | Ned-GTTTTGCGAGCTCATTGTCA (SEQ ID NO: 23) R-TGTGTGTGGTCTGTAGGCACT (SEQ ID NO: 24) | 60 | 8 | 0.80 | 0.80 | 0.77 | 0.01 | 5 | Gurcan et al. 2010a | B774 |
| B795 s$(TC)_5$ | $(TC)_8Ns(CT)_7Ns(CT)_{10}N$ | 296-332 | Fam-GACCCACAAACAATAACCTATCTC (SEQ ID NO: 25) R-TGGGCATCATCCAGGTCTA (SEQ ID NO: 26) | 60 | 12 | 0.76 | 0.74 | 0.74 | 0.01 | 9 | Gurcan et al. 2010a | B795 |
| C115 | $(TAA)_5(GAA)_{12}$ | 167-226 | Fam-ATTTTCCGCAGATAATACAGG (SEQ ID NO: 27) GTTTCCAGATCTGCCTCCATATAAT (SEQ ID NO: 28) | 60 | 14 | 0.80 | 0.80 | 0.77 | 0.00 | 4 | Bassil et al. 2005b, Gokirmak et al. 2009 | C115 |
| KG807 | $(TAAA)AA(TAAA)_2A(TAAA)_2$ | 226-248 | AAGCAAGAAAGGGATGGT (SEQ ID NO: 29) FAM-CTTACAGATAAATGGCTCAAA (SEQ ID NO: 30) | 54 | 4 | 0.67 | 0.78 | 0.60 | −0.07 | 11 | Gurcan and Mehlenbacher 2010 | KG807 |
| KG809 | $(AGG)_6$ | 333-345 | Hex-AGGCATCAGTTCATCCAA (SEQ ID NO: 31) F-GGAAGGTGAGAGAAATCAAGT (SEQ ID NO: 32) | 55 | 5 | 0.66 | 0.64 | 0.60 | 0.01 | 4 | Gurcan and Mehlenbacher 2010 | KG809 |
| KG811 | $(GA)_{17}$ | 240-278 | Ned-AAGGCGGCACTCGCTCAC(SEQ ID NO: 33) F-GAACAACTGAAGACAGCAAAG (SEQ ID NO: 34) | 58 | 12 | 0.83 | 0.82 | 0.81 | 0.01 | 2 | Gurcan and Mehlenbacher 2010 | KG811 |
| KG827 | $(CT)_{13}AA(CA)_7$ | 264-282 | Fam-AGAACTCCGACTAATAATCCTAACCCTTGC (SEQ ID NO: 35) GAGGGAGCAAGTCAAAGTTGAGAAGAAA (SEQ ID NO: 36) | 67 | 9 | 0.78 | 0.84 | 0.75 | −0.04 | 9 | Gurcan and Mehlenbacher 2010 | KG827 |
| KG830 | $(CT)_{14}GTATT(CA)_8$ | 279-311 | Ned-TGGAGGAAGTTTTGAATGGTAGTAGAGGA (SEQ ID NO: 37) AAAGCAACTCATAGCTGAAGTCCAATCA (SEQ ID NO: 38) | 67 | 9 | 0.79 | 0.78 | 0.76 | 0.00 | 9 | Gurcan and Mehlenbacher 2010 | KG830 |
| Soman-G | $(AAT)_5$ | 193-200 | Hex-TGGCGTTGCAACATATTCTC (SEQ ID NO: 39) | 54 | 3 | 0.60 | 0.98 | 0.51 | −0.27 | NA | unpublished | Soman-G |

TABLE 5-continued

Primers and annealing temperatures for the 21 microsatellite marker loci used to fingerprint 'McDonald' and other hazelnut cultivars.

| Locus | Repeat motif | Size | Primers 5'-3' (Forward above, Reverse below) | $T_s$ | n | He | Ho | PIC | r | LG | Reference | Locus |
|---|---|---|---|---|---|---|---|---|---|---|---|---|
| (=856-MS1-13) | | | R-GCCATCTTTAGAAAG TTCGATACAG (SEQ ID NO: 40) | | | | | | | | | |

Primers fluorescent tags are FAM, HEX and NED
Ta annealing temperature (° C.)
n number of alleles
He expected heterozygosity
Ho observed heterozygosity
PIC polymorphism information content
r estimated null allele frequency
LG linkage group; NA = not yet assigned
Reference for development and characterization

TABLE 6

Allele sizes in 'McDonald' and eight other hazelnut cultivars at 21 microsatellite loci.

| Locus | 'McDonald' | 'Tonda Pacifica' | 'Santiam' | 'Tonda Gentile delle Langhe' |
|---|---|---|---|---|
| A614 | 135/158 | 135/150 | 132/158 | 125/135 |
| A616 | 150/160 | 150/160 | 150/152 | 150/152 |
| A640 | 362/368 | 368/374 | 355/362 | 355/368 |
| B619 | 158/172 | 166/172 | 158/166 | 150/166 |
| B634 | 222/228 | 228/228 | 222/236 | 228/228 |
| B657 | 211/219 | 211/229 | 219/227 | 219/227 |
| B671 | 229/237 | 229/239 | 225/237 | 239/243 |
| B709 | 229/229 | 229/235 | 229/229 | 229/229 |
| B733 | 173/175 | 173/175 | 175/181 | 173/175 |
| B741 | 178/188 | 178/186 | 186/188 | 176/184 |
| B749 | 207/209 | 207/209 | 209/209 | 207/209 |
| B767 | 200/214 | 200/218 | 212/214 | 214/218 |
| B774 | 203/213 | 203/207 | 209/213 | 203/211 |
| B795 | 317/333 | 315/333 | 317/333 | 315/333 |
| C115 | 174/197 | 174/183 | 194/197 | 174/174 |
| KG807 | 252/252 | 228/252 | 242/252 | 238/252 |
| KG809 | 339/339 | 339/342 | 339/342 | 339/342 |
| KG811 | 245/267 | 245/257 | 257/267 | 257/267 |
| KG827 | 272/284 | 270/284 | 272/272 | 268/278 |
| KG830 | 291/295 | 291/295 | 291/295 | 291/295 |
| Soman-G | 196/200 | 196/200 | 196/200 | 196/200 |

| Locus | 'Barcelona' | 'Wepster' | 'Yamhill' | 'Dorris' |
|---|---|---|---|---|
| A614 | 125/132 | 135/158 | 132/158 | 132/158 |
| A616 | 144/152 | 152/160 | 150/150 | 150/152 |
| A640 | 355/374 | 368/374 | 355/368 | 372/374 |
| B619 | 158/172 | 166/172 | 158/172 | 158/166 |
| B634 | 228/228 | 228/228 | 236/236 | 228/228 |
| B657 | 219/223 | 227/229 | 219/229 | 211/227 |
| B671 | 225/229 | 239/249 | 225/243 | 229/249 |
| B709 | 227/235 | 229/235 | 229/229 | 229/229 |
| B733 | 173/175 | 173/175 | 181/185 | 173/181 |
| B741 | 178/186 | 178/186 | 178/186 | 178/186 |
| B749 | 209/209 | 207/209 | 209/209 | 207/207 |
| B767 | 214/240 | 200/242 | 214/238 | 214/218 |
| B774 | 203/207 | 203/207 | 203/211 | 203/207 |
| B795 | 333/333 | 333/333 | 333/333 | 333/333 |
| C115 | 174/194 | 183/194 | 197/216 | 194/216 |
| KG807 | 238/252 | 252/252 | 230/252 | 242/252 |
| KG809 | 339/339 | 342/342 | 348/348 | 339/348 |
| KG811 | 261/267 | 257/257 | 251/261 | 257/267 |
| KG827 | 282/284 | 270/282 | 268/282 | 272/284 |
| KG830 | 291/295 | 295/305 | 291/295 | 295/297 |
| Soman-G | 196/200 | 196/200 | 196/200 | 196/200 |

TABLE 6-continued

Allele sizes in 'McDonald' and eight other hazelnut cultivars at 21 microsatellite loci.

| Locus | 'York' | 'Felix' | 'Gasaway' |
|---|---|---|---|
| A614 | 124/158 | 138/143 | 143/158 |
| A616 | 144/152 | 150/152 | 150/150 |
| A640 | 363/374 | 368/372 | 362/368 |
| B619 | 158/166 | 158/166 | 172/176 |
| B634 | 228/236 | 228/236 | 222/234 |
| B657 | 221/223 | 219/227 | 225/229 |
| B671 | 243/249 | 229/237 | 237/249 |
| B709 | 229/233 | 229/233 | 229/229 |
| B733 | 173/181 | 175/181 | 175/175 |
| B741 | 178/186 | 186/186 | 186/188 |
| B749 | 209/209 | 207/207 | 207/209 |
| B767 | 236/238 | 214/214 | 214/214 |
| B774 | 203/209 | 203/213 | 203/209 |
| B795 | 333/333 | 321/333 | 317/319 |
| C115 | 197/197 | 197/216 | 216/219 |
| KG807 | 242/252 | 238/242 | 242/252 |
| KG809 | 339/348 | 339/348 | 339/348 |
| KG811 | 257/257 | 251/267 | 257/261 |
| KG827 | 268/272 | 272/284 | 272/282 |
| KG830 | 295/295 | 293/303 | 291/305 |
| Soman-G | 196/200 | 196/200 | 196/196 |

'McDonald' fingerprint same as both parents: 2
'McDonald' fingerprint same as one parent: 5
'McDonald' fingerprint different from both parents: 14

REFERENCES

Bassil N. V., Botta R., Mehlenbacher S. A. 2005a. Microsatellite markers in hazelnut: Isolation, characterization and cross-species amplification. J. Amer. Soc. Hort. Sci. 130:543-549.

Bassil N. V., Botta R., Mehlenbacher S. A. 2005b. Additional microsatellite markers of the European hazelnut. Acta Hort. 686:105-110.

Bassil N., Boccacci P., Botta R., Postman J. and Mehlenbacher S. A. 2012. Nuclear and chloroplast microsatellite markers to assess genetic diversity and evolution in hazelnut species, hybrids and cultivars. Genetic Resources and Crop Evolution (on-line) DOI 10.1007/s 10722-012-9857-z Boccacci P., Akkak A., Bassil N. V., Mehlenbacher S. A., Botta R. 2005. Characterization and evaluation of microsatellite loci in European hazelnut (*C. avellana*) and their transferability to other *Corylus* species. Molec. Ecol. Notes 5:934-937.

Boccacci P., Akkak, A. and Botta, R. 2006. DNA typing and genetic relations among European hazelnut (*Corylus avellana* L.) cultivars using microsatellite markers. Genome 49:598-611.

Gökirmak T., Mehlenbacher S. A., Bassil N. V. 2009. Characterization of European hazelnut (*Corylus avellana*) cultivars using SSR markers. Genetic Resources and Crop Evolution 56:147-172.

Gürcan, K. and S. A. Mehlenbacher. 2010. Transferability of microsatellite markers in the Betulaceae. J. Amer. Soc. Hort. Sci. 135:159-173.

Gürcan, K. and S. A. Mehlenbacher. 2010. Development of microsatellite marker loci for European hazelnut (*Corylus avellana* L.) from ISSR fragments. Molecular Breeding 26:551-559. (available on-line as DOI 10.1007/s11032-010-9464-7)

Gürcan, K., S. A. Mehlenbacher and V. Erdogan. 2010a. Genetic diversity in hazelnut cultivars from Black Sea countries assessed using SSR markers. Plant Breeding 129:422-434. (available on-line doi :10. 1111/j. 1439-0523. 2009. 01753. x).

Gürcan, K., S. A. Mehlenbacher, R. Botta and P. Boccacci. 2010b. Development, characterization, segregation, and mapping of microsatellite markers for European hazelnut (*Corylus avellana* L.) from enriched genomic libraries and usefulness in genetic diversity studies. Tree Genetics and Genomes 6:513-531. (available on-line as DOI: 10.1007/s11295-010-0269-y)

Mehlenbacher, S. A., D. C. Smith, R. L. McCluskey and M. M. Thompson. 2011. 'Tonda Pacifica' hazelnut. HortScience 46:505-508.

Mehlenbacher, S. A., A. N. Azarenko, D. C. Smith, and R. L. McCluskey. 2007. 'Santiam' hazelnut. HortScience 42:715-717.

Sathuvalli, V. R. and S. A. Mehlenbacher. 2012. Characterization of American hazelnut (*Corylus americana*) accessions and *Corylus americana*×*Corylus avellana* hybrids using microsatellite markers. Genetic Resources and Crop Evolution 59:1055-1075. DOI 10.1007/s10722-011-9743-0.

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1

tggcagagct ttgtcagctt                                                  20


<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2

gcagtggagg attgctgact                                                  20


<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3

cactcatacc gcaaactcca                                                  20


<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4

atggcttttg cttcgttttg                                                  20
```

-continued

<210> SEQ ID NO 5
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 5 tgcctctgca gttagtcatc aaatgtagg 29

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6 cgccatataa ttgggatgct tgttg 25

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7 agtcggctcc ccttttctc 19

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8 gcgatctgac ctcatttttg 20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9 cctgcatcca ggactcatta 20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10 gtgcagaggt tgcactcaaa 20

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide -continued

<400> SEQUENCE: 11 ttgccagtgc atactctgat g 21

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12 accagctctg ggcttaacac 20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13 ccaagcacga atgaactcaa 20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14 gcgggttctc gttgtacact 20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15 caccctcttc accacctcat 20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16 catcccctgt tggagttttc 20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17 gttcacaggc tgttgggttt 20

-continued

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18 cgtgttgctc atgtgttgtg 20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19 ggctgacaac acagcagaaa 20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20 tcggctaggg ttagggtttt 20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21 ccaccaactg tttcacacca 20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22 gcgaaatgga gctcttgaac 20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23 gttttgcgag ctcattgtca 20

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide -continued

<400> SEQUENCE: 24 tgtgtgtggt ctgtaggcac t 21

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25 gacccacaaa caataaccta tctc 24

<210> SEQ ID NO 26
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 26 tgggcatcat ccaggtcta 19

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27 attttccgca gataatacag g 21

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28 gtttccagat ctgcctccat ataat 25

<210> SEQ ID NO 29
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 29 aagcaagaaa gggatggt 18

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30 cttacagata aatggctcaa a 21

-continued

<210> SEQ ID NO 31
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 31 aggcatcagt tcatccaa 18

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 32 ggaaggtgag agaaatcaag t 21

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 33 aaggcggcac tcgctcac 18

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34 gaacaactga agacagcaaa g 21

<210> SEQ ID NO 35
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 35 agaactccga ctaataatcc taacccttgc 30

<210> SEQ ID NO 36
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 36 gagggagcaa gtcaaagttg agaagaaa 28

<210> SEQ ID NO 37
<211> LENGTH: 29
<212> TYPE: DNA
<213> ORGANISM: Artificial Sequence
<220> FEATURE:
<223> OTHER INFORMATION: Synthetic oligonucleotide -continued

<400> SEQUENCE: 37 tggaggaagt tttgaatggt agtagagga 29

<210> SEQ ID NO 38
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 38 aaagcaactc atagctgaag tccaatca 28

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39 tggcgttgca acatattctc 20

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 40 gccatcttta gaaagttcga tacag 25

We claim:

1. A new and distinct cultivar of *Corylus* plant as herein illustrated and described.

* * * * *

FIG. 12A

Phenology Chart 1. Time of female receptivity (bottom, red) and pollen shed (top, green) of OSU 880.027 and other hazelnut cultivars (Dec 2011 - Mar 2012).

| | Dec | | Jan | | | | | | Feb | | | | | | March | | | |
|---|---|---|---|---|---|---|---|---|---|---|---|---|---|---|---|---|---|---|
| Genotype | 21-25 | 26-31 | 1-5 | 6-10 | 11-15 | 16-20 | 21-25 | 26-31 | 1-5 | 6-10 | 11-15 | 16-20 | 21-25 | 26-32 | 1-5 | 6-10 | 12-21 | 25-33 |
| Wepster | | | | | | | | 10 | 95-30 | -50 | -90 | | | | | | | BB |
| (1, 2) | Rd+3 | Rd+3fl | | Rd/l+2 | l+3 | l+3 | l+3/S | | l+3/S+3 | | | | | | | | | |
| 06 | | | | | | dk | | | blk | | | Red/dk | | | | | | |
| T. di Giffoni | 1st | | | 5 | 10 | 25 | 75 | -90 | -90 | BB | Leaves 1/4" | | | | | | | |
| (2, 23) | Rd/l | | l+2/S | l+2/S+2 | MS | | | MS | MS | | | | | | | | | |
| 02 | | | | | dk | | | dk | blk | | | | | | | | | |
| Yamhill | | | | | 20 | 50 | 95 | 100-50 | -90 | done | | gr lip | | | BB | | | |
| (3, 29) | Rd | | Rd+3fl | | | MS+2 | l+2/S+2 | | l+2/S+3 | MS | MS | | | | | | | |
| 109-1 '07 | | | | | | Red | Red/dk | | dk | | blk | | | | | | | |
| Dorris | | | | | | 10 | 50 | 95-20 | -95 | done | | | | | | | | BB |
| (1, 12) | | | | Rd+2 | Rd+3 | | | Rd/l+3 | l+2/S | l+2/S+2 | MS | | | | | | | |
| 06 | | | | | blk | | | | dk/blk | | blk | | | | | | | |
| York | | | | | | | | 30 | 100-50 | -80 | | | | | | | | BB |
| (2, 21) | | | Rd+2 | | Rd+3 | Rd+3fl | Rd/l+3 | | l+3/S | | l+3/S+2 | | MS | | | | | |
| 06 | | | | | dk | | dk | | dk | | blk | | blk | | | | | |
| Lewis | | | | | | 1st | 35 | 90-20 | 90-30 | | -80 | | BB | | | | | |
| (3, 8) | | | | 1st Rd | | | Rd/l | l+2 | l+3 | | l | l+2/S+2 | | | | | | |
| 02 | | | | | | | Few female | Red | Red | | Red | Red | | | | | | |
| Santiam | | | | | | 1st | 20 | 100-50 | done | | | | | | | BB | | |
| (3, 15) | Rd+2 | | | Rd+2 | Rd+3 | Rd+3 | Rd+2/l+3 | | l+3/S | | l+2/S+3 | MS | | | | | | |
| 06 | Black | | | | blk | blk | | | blk | | blk | blk | | | | | | |

Female flower stages: RD = Red dot; l = styles protruding ~1-3mm, straight; FS = First appearance of 'spiders' (reflexed styles), and MS = majority of flowers are in 'spider' stage.

Green = Pollen shed (a minus sign in front of the number indicates the percent of catkins that have already shed out); drop = 50% catkins dropped.

Red = Female flowers, red, blk (black), dk (dark, not quite red, not yet black).

BB = date of leaf budbreak.

FIG. 12B

Phenology Chart 1. Time of female receptivity (bottom, red) and pollen shed (top, green) of OSU 888.027 and other hazelnut cultivars (Dec 2011 - Mar 2012).

| | Dec | | Jan | | | | | | Feb | | | | | | March | | | |
|---|---|---|---|---|---|---|---|---|---|---|---|---|---|---|---|---|---|---|
| Genotype | 21-28 | 28-31 | 1-5 | 6-10 | 11-15 | 16-20 | 21-25 | 26-31 | 1-5 | 6-10 | 11-15 | 16-20 | 21-25 | 26-29 | 1-5 | 6-10 | 12-21 | 25-31 |
| Wepster | | | | | | | | 10 | 95-20 | -50 | -80 | | | | | | | BB |
| (1, 2) | Rd+3 | Rd+3R | | Rd/I+2 | I+3 | I+3 | I+3/S | | I+3/S+3 | | | | | | | | | |
| 06 | | | | | | dk | | | blk | | | Red/dk | | | | | | |
| Sacajawea | | | | | | 1st | 10 | 75 | 100-50 | -80 | | | | | BB | | | |
| (1, 22) | Rd+3R | | Rd/I+2 | I+2/S | I/S+2 | | MS | | MS | | MS | MS | | | | | | |
| 06 | Red | | Red | | Red/dk | | Red/dk | | | | dk/blk | blk | | | | | | |
| 888.027 | | | | | | 5 | 20 | 100-40 | -80 | | | | | | | | | BB |
| (2, 15) | Rd | | Rd+2 | Rd/I | Rd+2R | I+2 | I+3/S | | I+2/S+3 | MS | MS | | | | | | | |
| 06 | | | | | dk | | dk | | dk | dk | dk/blk | | | | | | | |
| Hall's Giant | | | | | | 1st | 25 | 80 | 95-10 | -40 | 100-60 | -80 | | | | | | BB |
| (5, 15) | | | | | | Rd | Rd | Rd/I | I+3 | I+3/S+2 | MS | MS | | | | | | |
| 02 | | | | | | | | | Red | | Red | dk | | | | | | |
| Gamma | | | | | | | | 85 | 90-20 | -70 | | | | | | | | BB |
| (2, 10) | | | | | Rd | | Rd/I | Rd+3R+2 | I+2/S | | I+2/S+2 | | | | | | | |
| 09 | | | | | | | Red | | Red | | Red | blk | | | | | | |
| Felix | | | | | | | | 1st | 10 | 30 | 50 | 95-40 | | | | | | BB |
| (15, 21) | Rd/I | | | | Rd+2R+2 | | I+2/S | | I+3/S+2 | | | | | | | | | |
| 07 | | | | | dk | | Red | | Red | | Red/dk | | | | | | | |
| Jefferson | | | | | | | | 1st | 10 | 75 | 100-50 | -80 | | | | | | BB |
| (1, 3) | | | | | 1st Rd | | | Rd | Rd+2 | Rd | Rd/I+2 | I+2/S+2 | | | | | | |
| 06 | | | | | | | | | | | | Red | | | | | | |

Female flower stages: RD = Red dot; I = styles protruding ~1-3mm, straight; FS = First appearance of 'spiders' (reflexed styles), and MS = majority of flowers are in 'spider' stage.

Green = Pollen shed (a minus sign in front of the number indicates the percent of catkins that have already shed out); drop = 50% catkins dropped.

Red = Female flowers; red, blk (black), dk (dark, not quite red, not yet black).

BB = date of leaf budbreak.

FIG. 13A

Phenology Chart 2. Bloom stage and pollen shed of hazelnut cultivars, pollinizers and selections (Dec 2012 - Mar 2013)

| | Dec | | Jan | | | | | | Feb | | | | | | March | | | |
|---|---|---|---|---|---|---|---|---|---|---|---|---|---|---|---|---|---|---|
| | 21-25 | 26-31 | 1-5 | 6-10 | 11-15 | 16-20 | 21-25 | 26-31 | 1-5 | 6-10 | 11-15 | 16-20 | 21-25 | 26-31 | 1-5 | 6-10 | | |
| Genotype | 22-Dec | 30-Dec | 4-Jan | 8-Jan | 15-Jan | 20-Jan | 25-Jan | 30-Jan | 5-Feb | 10-Feb | 15-Feb | 19-Feb | 25-Feb | 28-Feb | 7-Mar | 11-Mar | 18-Mar | 27-Mar |
| **Area 11** | | | | | | | | warmdby | | | | | | | | | | |
| T. Pacifica | | | | 5 | | | 10 | 70 | 100-40 | -80 | | Gr tip | | | BB | | | |
| (1, 2) | | Rd | Rd+3 | Rd8+2 | | | Rd / I+3 | I+3 | I / S+3 | MS | | | MS | | | | | |
| 30 | | | | | | | Dark | | | Red/dk | | | Dark | | | | | |
| **Area 12** (planted 1990) | | | | | | | | | | | | | | | | | | |
| TGDL | 30 | 30 | 75 | -90 | -95 | | | | | | Gr tip | 85 | | | | | | |
| (2, 7) | | Rd | I+2 / S+2 | | | | | MS | | MS | MS | | MS | | | | | |
| R01.05 | | | Red | | | | | Red | | Red/dk | Dark | | Black | | | | | |
| **Area 12** (planted 2007) | | | | | | | | | | | | | | | | | | |
| Yamhill | | | | | | | 1st | 25 | 75 | 100-20 | -90 | | Gr tip | BB | | | | |
| (8, 26) | | Rd | Rd+2 | Rd / I | n/c | n/c | Rd8+2 | I+2/S+2 | n/c | MS | | | MS | | | | | |
| 109-1 '07 | | | | Red | | | Red | Red | | Red/dk | | | Black | | | | | |
| **Area 17** | | | | | | | | | | | | | | | | | | |
| Dorris | | | | | | | | 30 | 90 | 100 -40 | | | | | | | | |
| (1, 12) | Rd+3 | Rd+2 / I | | Rd | | | Rd+3 | I+3 / S | I+2 / S+2 | | | | MS | MS | | Gr tip | BB | |
| 06 | | | | | | | Dark | | | | | | dk/blk | Black | | | | |
| York | | | | | | | | 1st | 25 | 75 | 100-30 | -90 | | Gr tip | | | BB | |
| (2, 21) | Rd+2 | Rd+3 | | | | Rd+3 / I | Rd+2 / I+2 | I+3 / S | | MS+3 | | | I / S+3 | | | | | |
| 06 | | | | | | | Dk | Red | | Dk | | | Dark | Black | | | | |
| 880.027 | | | | | | | | 25 | 75 | -90 | | | | Gr tip | | BB | | |
| (2, 15) | Rd+2 | Rd+3 | | | | Rd+2 / I | Rd / I+3 | I+2 / S+3 | MS | | MS | | | | | | | |
| 06 | | | | | | | Red | | Red | | Dark | | | | | | | |
| Wepster | | | | | | | | 1st | 20 | 25 | -80 | | | Gr tip | | | BB | |
| (1, 2) | Rd+3d | Rd+3d | | Rd+3d | | | Rd8+3 | MS+3 | | | MS | | | | | | | |
| 06 | | | | Red | | | Red | | | | Dark | | | | | | | |

Flower stages: RD = Red dot, I = styles protruding ~1-3mm, straight; FS = First appearance of 'spiders' or flowers with reflexed styles, and MS = majority of flowers are in 'spider' or fully reflexed stage.

Green = Pollen shed (a minus sign in front of the number indicates A362the percent of catkins that have already shed out); drop = 50% catkins dropped.

Red = Female flowers; red, blk (black), dk (dark, not quite red, not yet black).

FIG. 13B

Phenology Chart 2. Bloom stage and pollen shed of hazelnut cultivars, pollinizers and selections (Dec 2012 - Mar 2013).

| | Dec | | Jan | | | | | | Feb | | | | | | March | | | |
|---|---|---|---|---|---|---|---|---|---|---|---|---|---|---|---|---|---|---|
| | 21-25 | 26-31 | 1-5 | 6-10 | 11-15 | 16-20 | 21-25 | 26-31 | 1-5 | 6-10 | 11-15 | 16-20 | 21-25 | 26-31 | 1-5 | 6-10 | | |
| Genotype | 22-Dec | 30-Dec | 4-Jan | 8-Jan | 15-Jan | 20-Jan | 25-Jan | 30-Jan | 5-Feb | 10-Feb | 15-Feb | 19-Feb | 25-Feb | 28-Feb | 7-Mar | 11-Mar | 18-Mar | 27-Mar |
| **Area 17** | | | | | | | | | | | | | | | | | | |
| Santiam | | | | | | | | 65 | 100 | | | | | Gr tip | BB | | | |
| (3, 15) | | | Rd | | Rd+2 | | Rd / I+2 | I+2 / S+2 | I / S+3 | MS | | | MS | | | | | |
| 06 | | | Dark | | | | dk | | | dk | | | blk | | | | | |
| Yamhill | | | | | | | | 20 | 60 | 95 | -60 | | Gr tip | | BB | | | |
| (8, 26) | Rd+3 | Rd+3 / I | | I+3 / S | | | I+3 / S | I / S+3 | S+3 | MS | MS | | | | | | | |
| 06 | | | | | | | Red | | | Red | Dark | | | | | | | |
| Jefferson | | | | | | | | | | 40 | 100 | -60 | | | | Gr tip | BB 3/22 | |
| (1, 3) | | | | | 1st Rd | | | Rd+2 / I+2 | | I+2 | | I+3 | I+2 / S+2 | MS | | MS | | |
| 06 | | | | | | | | Red | | Red | | Red/dk | Dark | | | Dark | | |
| Sacajawea | | | | | | | | 1st | 20 | 100 | -90 | | Gr tip | BB | | | | |
| (1, 22) | I+3 | | I+3 | I+3/S+2 | | | | MS | | | MS | | MS | | | MS | | |
| 06 | | | Red | | | | | Red | | | Dark | | dk/blk | | | Black | | |
| Eta / VR | | | | | | | | | | | 30 | 70 | 100-30 | -80 | | | BB 3/22 | |
| (11, 26) | | | | | 1st Rd | | | Rd | | Rd/I+2 | I+2/S | | I/S+3 | | | MS | | |
| 06 | | | | | | | | | | Red | | | Red | | | Red/Dark | | |
| Theta / VR | | | | | | | | | | | | | 5 | 40 | 75 | 90 | -75 | BB |
| (5, 15) | 1st Rd | | Rd | | Rd+2 | | | Rd/I | | I+3 | I+3/S | | | | | MS | Gr tip | post 3/22 |
| 06 | | | | | | | | | | | Red | | | | | Red / Black | | |
| **A 11 South** | | | | | | | | | | | | | | | | | | |
| Felix | | | | | | | | | 5 | 25 | 80 | 100-40 | -90 | | Gr tip | | BB 3/22 | |
| (15, 21) | Rd | Rd+2 | | Rd+3 | | | Rd / I | | I / S+3 | | MS | | MS | | | | | |
| 07 | | | | | | | dk | Red | Red/dk | | | | Dk/Blk | | | | | |

Phenology Chart 2. Bloom stage and pollen shed of hazelnut cultivars, pollinizers and selections (Dec 2012 - Mar 2013).